United States Patent
Kobayashi et al.

(10) Patent No.: US 9,316,912 B2
(45) Date of Patent: *Apr. 19, 2016

(54) POSITIVE TYPE RESIST COMPOSITION FOR USE IN LIQUID IMMERSION EXPOSURE AND A METHOD OF FORMING THE PATTERN USING THE SAME

(71) Applicant: FUJIFILM Corporation, Minato-Ku, Tokyo (JP)

(72) Inventors: Hiromi Kobayashi, Shizuoka (JP); Haruki Inabe, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/449,415

(22) Filed: Aug. 1, 2014

(65) Prior Publication Data

US 2015/0205205 A1 Jul. 23, 2015

Related U.S. Application Data

(63) Continuation of application No. 13/782,148, filed on Mar. 1, 2013, now Pat. No. 8,828,643, which is a continuation of application No. 13/228,135, filed on Sep. 8, 2011, now Pat. No. 8,426,109, which is a
(Continued)

(30) Foreign Application Priority Data

Jul. 7, 2004 (JP) .................................. 2004-200679

(51) Int. Cl.
*G03F 7/004* (2006.01)
*G03F 7/039* (2006.01)
(Continued)

(52) U.S. Cl.
CPC .............. *G03F 7/0397* (2013.01); *C07C 69/54* (2013.01); *G03F 7/0045* (2013.01);
(Continued)

(58) Field of Classification Search
CPC ..... G03F 7/004; G03F 7/0045; G03F 7/0046; G03F 7/0392; G03F 7/0395; G03F 7/397; G03F 7/2041; H01L 21/0274; C07C 69/54
USPC ................................................ 430/270.1, 322
See application file for complete search history.

(56) References Cited

U.S. PATENT DOCUMENTS 6,589,705 B1 7/2003 Sato et al.
6,627,391 B1 9/2003 Ito et al.
(Continued)

FOREIGN PATENT DOCUMENTS

EP 1 347 335 A1 9/2003
EP 1 376 232 A1 1/2004
(Continued)

OTHER PUBLICATIONS

Notification of Reasons for Refusal dated Apr. 13, 2010 in Japanese Application No. 2005-196529.
(Continued)

*Primary Examiner* — Amanda C Walke
(74) *Attorney, Agent, or Firm* — Sughrue Mion, PLLC

(57) ABSTRACT

A positive type resist composition for use in liquid immersion exposure comprises: (A) a resin having a monocyclic or polycyclic cycloaliphatic hydrocarbon structure, the resin increasing its solubility in an alkali developer by an action of acid; (B) a compound generating acid upon irradiation with one of an actinic ray and a radiation; (C) an alkali soluble compound having an alkyl group of 5 or more carbon atoms; and (D) a solvent.

16 Claims, 1 Drawing Sheet

Related U.S. Application Data continuation of application No. 12/325,472, filed on Dec. 1, 2008, now Pat. No. 8,039,197, which is a continuation of application No. 11/175,366, filed on Jul. 7, 2005, now Pat. No. 7,531,287.

(51) Int. Cl.
  *H01L 21/027* (2006.01)
  *C07C 69/54* (2006.01)
  *G03F 7/20* (2006.01)

(52) U.S. Cl.
  CPC ........... *G03F 7/0046* (2013.01); *G03F 7/0392* (2013.01); *G03F 7/0395* (2013.01); *G03F 7/2041* (2013.01); *H01L 21/0274* (2013.01); *Y10S 430/106* (2013.01); *Y10S 430/114* (2013.01); *Y10S 430/146* (2013.01)

(56) References Cited

U.S. PATENT DOCUMENTS

| | | | |
|---|---|---|---|
| 6,788,477 | B2 | 9/2004 | Lin |
| 6,824,956 | B2 | 11/2004 | Sato |
| 7,087,356 | B2 | 8/2006 | Khojasteh et al. |
| 7,189,492 | B2 | 3/2007 | Kodama et al. |
| 7,252,924 | B2 | 8/2007 | Yamanaka |
| 7,569,326 | B2 | 8/2009 | Ohsawa et al. |
| 8,039,197 | B2 | 10/2011 | Kanda et al. |
| 8,426,109 | B2 | 4/2013 | Kanda et al. |
| 2003/0224287 | A1 | 12/2003 | Fujimori |
| 2003/0235781 | A1 | 12/2003 | Shida et al. |
| 2004/0197707 | A1 | 10/2004 | Yamanaka |
| 2005/0019690 | A1 | 1/2005 | Kodama |
| 2005/0069819 | A1 | 3/2005 | Shiobara |
| 2005/0094125 | A1 | 5/2005 | Arai |
| 2005/0208420 | A1 | 9/2005 | Ober et al. |
| 2005/0227173 | A1 | 10/2005 | Hatakeyama et al. |
| 2005/0260519 | A1 | 11/2005 | Berger et al. |
| 2006/0008736 | A1 | 1/2006 | Kanda et al. |
| 2006/0141400 | A1 | 6/2006 | Hirayama et al. |
| 2006/0172225 | A1 | 8/2006 | Mintz et al. |
| 2006/0246373 | A1 | 11/2006 | Wang |
| 2007/0134593 | A1 | 6/2007 | Hirayama et al. |
| 2009/0181323 | A1 | 7/2009 | Kanda et al. |
| 2015/0079508 | A1* | 3/2015 | Ito et al. ........................ 430/18 |

FOREIGN PATENT DOCUMENTS

| | | |
|---|---|---|
| EP | 1 505 439 A2 | 2/2005 |
| EP | 1 517 179 A1 | 3/2005 |
| JP | 57-153433 A | 9/1982 |
| JP | 7-220990 A | 8/1995 |
| JP | 10-303114 A | 11/1998 |
| JP | 2000-035664 A | 2/2000 |
| JP | 2002-62640 A | 2/2002 |
| JP | 2003-156845 A | 5/2003 |
| JP | 2003-262952 A | 9/2003 |
| JP | 2003-270791 A | 9/2003 |
| JP | 2003-302762 A | 10/2003 |
| JP | 2003-302763 A | 10/2003 |
| JP | 2003-330195 A | 11/2003 |
| JP | 2004-77817 A | 3/2004 |
| JP | 2004-117677 A | 4/2004 |
| JP | 2004-126302 A | 4/2004 |
| JP | 2004-238304 A | 8/2004 |
| JP | 2005-128416 A | 5/2005 |
| JP | 2005-320516 A | 11/2005 |
| JP | 2006-48029 A | 2/2006 |
| KR | 10-2006-0040715 A | 5/2006 |
| KR | 10-2006-0046646 A | 5/2006 |
| WO | 02/44814 A2 | 6/2002 |
| WO | 03-099782 A2 | 12/2003 |
| WO | 2004/074937 A1 | 9/2004 |
| WO | 2005/008336 A2 | 1/2005 |

OTHER PUBLICATIONS

Notification of Reasons for Refusal dated Sep. 7, 2010 in Japanese Application No. 2005-196529.
Office Action dated Dec. 7, 2010 in Japanese Application No. 2005-196529.
Communication dated Nov. 15, 2011, issued by the Japanese Patent Office in Japanese Patent Application No. 2010-135540.
Office Action dated Feb. 29, 2012 in Korean Patent Application No. 10-2005-0061060.
Office Action dated Jul. 25, 2012 in Korean Patent Application No. 10-2012-0049158.
Office Action dated Sep. 19, 2011 in Taiwanese Application No. 094122785.
J. A. Hoffnagle et al., Liquid Immersion Deep-Ultraviolet Interferometric Lithography, J. Vac. Sci. Technol, B., Nov./Dec. 1999, pp. 3306-3309, vol. 17, No. 6.
B. J. Lin, Semiconductor Foundry, Lithography, and Partners, Proceedings of SPIE, 2002, pp. 11-24. vol. 4688.
Shinji Kishimura et al., Resist interaction in 193-/157-nm immersion lithography (2004), Proceedings of SPIE, vol. 5376, pp. 44-55.
William Hinsberg et al., Liquid Immersion Lithography—Evaluation of Resist Issues (2004), Proceedings of SPIE, vol. 5376, pp. 21-33.
European Search Report dated Feb. 20, 2006.
Communication dated Nov. 15, 2013, issued by the Korean Intellectual Property Office in Korean Application No. 10-2013-0048700.
Office Action issued Aug. 28, 2013, by the Korean Intellectual Property Office in Korean Application No. 10-2012-0049158.
Office Action dated Jan. 31, 2013 in Korean Patent Application 10-2012-0049158.
Office Action dated Jul. 17, 2013, issued by the Korean Intellectual Property Office in Korean Application No. 10-2013-0048700.

* cited by examiner

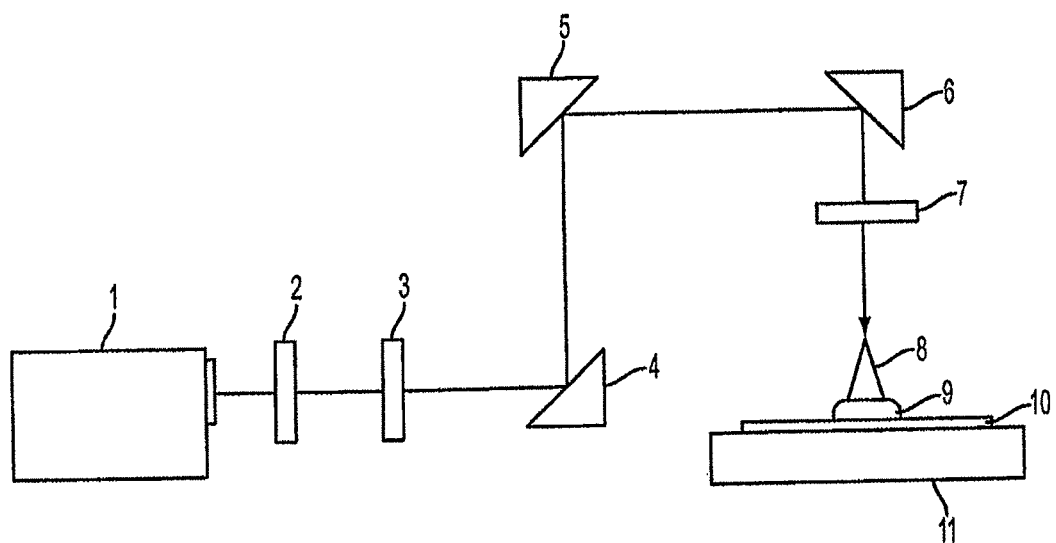

POSITIVE TYPE RESIST COMPOSITION FOR USE IN LIQUID IMMERSION EXPOSURE AND A METHOD OF FORMING THE PATTERN USING THE SAME

CROSS-REFERENCE TO RELATED APPLICATIONS

This is a Continuation application of U.S. application Ser. No. 13/782,148 filed Mar. 1, 2013, which is a Continuation of U.S. application Ser. No. 13/228,135 filed Sep. 8, 2011, now U.S. Pat. No. 8,426,109, which is a Continuation of U.S. application Ser. No. 12/325,472 filed Dec. 1, 2008, now U.S. Pat. No. 8,039,197, which is a Continuation of application Ser. No. 11/175,366 filed Jul. 7, 2005, now U.S. Pat. No. 7,531,287, which claims priority under 35 U.S.C. §119 from JP 2004-200679, filed Jul. 7, 2004, the disclosures of all of the above applications are incorporated herein by reference.

BACKGROUND OF THE INVENTION

1. Field of the Invention

The present invention concerns a positive type resist composition for use in the step of manufacturing a semiconductors such as IC, and lithographic steps for the manufacture of circuit substrates, for example, in liquid crystals and thermal heads and other photo applications, as well as a method of forming a pattern using the same. Particularly, it relates to a positive type resist composition suitable to exposure by a liquid immersion type projection exposure systems using far UV-light at a wavelength of 300 nm or less as a light source, as well as a method of forming the pattern using the same.

2. Description of the Related Art

Along with refinement of semiconductor devices, development has been conducted for making the wavelength of a exposure light source shorter and making the numerical aperture of a projection lens higher (high NA), and a developing apparatus having NA of 0.84 using, as a light source, an ArF excimer laser having a wavelength at 193 nm has been developed at present. The resolution and the focal depth can be represented by the following equations.

$$(\text{Resolution}) = k_1 \cdot (\lambda/\text{NA})$$

$$(\text{Focal depth}) = \pm k_2 \cdot \lambda/\text{NA}^2,$$

where $\lambda$ is wavelength of an exposure light source, NA is a numeral aperture of a projection lens, and $k_1$ and $k_2$ are coefficients related to a process.

An exposure apparatus using an $F_2$ excimer laser having a wavelength at 157 nm as a light source has now under investigation for attaining higher resolution by making the wavelength further shorter but since the lens material used for the exposure apparatus and the material used for the resist are extremely restricted for shorting the wavelength, reduction of the manufacturing cost for the apparatus and the material and for stabilization of quality are extremely difficult, which have resulted in the possibility that exposure apparatus and resist having sufficient performance and stability can not be in time for the requested term.

As a technique for improving the resolution of an optical microscope, a so-called liquid immersion method has been known so far of filling a liquid of high refractive index (hereinafter also referred to as "liquid immersion solution") between a projection lens and a specimen.

For the "effect of liquid immersion", the resolution and the focal depth described above can be represented by the following equations in a case of liquid immersion assuming the wavelength of exposure light in air as $\lambda_0$, the reflective index of the liquid immersion solution to air as n, a conversing semi-angle of a light as $\theta$, and $NA_0 = \sin \theta$:

$$(\text{Resolution}) = k_1 \cdot (\lambda_0/n)/NA_0$$

$$(\text{Focal depth}) = \pm k_2 \cdot (\lambda_0/n)/NA_0^2$$

That is, the effect of the liquid immersion is equivalent with that in the case of using 1/n exposure wavelength. In other words, the focal depth can be increased to n times by liquid immersion in a case of a projection optical system of identical NA.

This is effective to all sorts of pattern shapes and, further, can be combined with super resolution technique such as a phase shift method, a modified illumination method, etc. which have been under investigation at present.

Examples of apparatus applying the effects described above to the transfer of fine patterns of semiconductor devices are described in JP-A No. 57-153433, JP-A No. 7-220990, etc., but they do not described resists suitable to the liquid immersion technique.

JP-A No. 10-303114 points out that control for the refractive index of the liquid immersion solution is important since the change of the refractive index of the liquid immersion solution causes degradation of projected images due to spherical aberration of exposure apparatus and discloses control of the temperature coefficient of the refractive index of the liquid immersion solution to a certain range, and water with addition of additives for lowering the surface tension or increasing the surface activity as a suitable liquid immersion solution. However, disclosure of the additives or the resist suitable to the liquid immersion exposure technique is not discussed.

Development of the recent liquid immersion exposure technique is reported, for example, in Bulletin of the International Society for Optical Engineering (Proc. SPIE), 2002, Vol. 4688, p 11, and J. Vac. Sci. Tecnol. B, 17 (1999), etc. In a case of using an ArF excimer laser as a light source, it is considered that pure water (refractive index at 193 nm of 1.44) is considered most prospective as a liquid immersion solution with a view point of handling safety, and transmittance and refractive index at 193 nm.

In a case of using an $F_2$ excimer laser as a light source, while a solution containing fluorine has been considered in view of the balance between the transmittance and the refractive index at 157 nm, no satisfactory solution in view of the circumstantial safety and the refractive index has yet been found. In view of the degree of the effect of liquid immersion and the degree of completion of the resist, it is considered that the liquid immersion exposure technique will be adopted at first to the ArF exposure apparatus.

Since the resist for use in a KrF excimer laser (248 nm), an image forming method of chemical amplification is used as a method of forming resist images in order to compensate the lowering of sensitivity caused by light absorption. Referring to the example of the image forming method of the positive type chemical amplification, this is an image forming method of decomposing an acid generator in an exposed area by exposure to generate an acid, converting the alkali insoluble group into an alkali soluble group by Post Exposure Bake (PEB) using the generated acid as a reaction catalyst and removing the exposed area by alkali development.

In the liquid immersion exposure, a resist film is exposed through a photomask in a state where a space between the resist film and the optical lens is filled with the dipping solution (also referred to as a liquid immersion solution) to transfer the pattern of the photomask to the resist film. However, it is anticipated that the dipping solution permeates inside the resist film thereby giving undesired effect on the performance of the resist.

When a chemical amplification resist is applied to the liquid immersion exposure technique, the acid on the resist surface generated during exposure is transferred to the liquid immersion solution to change the concentration of the acid at the surface of the exposed area. It is considered that this is extremely similar with acid deactivation on the surface of the exposure area caused by basic contamination of an extremely small amount at several ppb level from the circumstance during Post Exposure time Delay (PED) which caused a significant problem in the initial stage of the development of the chemical amplification type positive resist but the effect and the mechanism given by the liquid immersion exposure on the resistor have not yet been apparent.

On the other hand, in a case of applying chemical amplification type resist having no problem in the lithography by usual exposure to the pattern formation by the liquid immersion exposure, it has been found problems that development defects and development residues (scums) are formed, or leaching of the resist to the liquid immersion solution occurs.

SUMMARY OF THE INVENTION

In view of the foregoing problems in the prior art, the present invention intends to provide a positive type resist composition suitable to liquid immersion exposure capable of suppressing the formation of development defects and scums, with preferably less leaching of resist ingredients to the liquid immersion solution upon pattern formation by liquid immersion exposure, as well as a method of forming a pattern using the same.

The present invention provides a positive type resist composition for use in liquid immersion exposure of the following constitution, as well as a method of forming the pattern using the same, by which the foregoing object of the invention can be attained.

(1) A positive type resist composition for use in liquid immersion exposure comprising:
(A) a resin having a monocyclic or polycyclic cycloaliphatic hydrocarbon structure, the resin increasing its solubility in an alkali developer by an action of acid;
(B) a compound generating an acid upon irradiation with one of an actinic ray and a radiation;
(C) an alkali soluble compound having an alkyl group of 5 or more carbon atoms; and
(D) a solvent.
(2) A positive type resist composition for use in liquid immersion exposure as described in (1) above, wherein the alkali soluble compound (C) has at least one or more of fluorine atom.
(3) A positive type resist composition for use in liquid immersion exposure as described in (2) above, wherein the alkyl group of the alkali soluble compound (C) has at least one or more of fluorine atom.
(4) A positive type resist composition for use in liquid immersion exposure as described in any one of (1) to (3) above, wherein the alkali soluble compound (C) has an alcoholic hydroxyl group in which the alcohol moiety is a fluorinated alcohol.
(5) A positive type resist composition for use in liquid immersion exposure as described in any one of (1) to (4) above, wherein the alkali soluble compound (C) has a carboxylic group.
(6) A method of forming a pattern comprising: forming a resist film by a resist composition as described in any one of (1) to (5) above; subjecting the resist film to liquid immersion exposure, so as to form a exposed resist film; and developing the exposed resist film.

BRIEF DESCRIPTION OF THE DRAWINGS

FIG. 1 is a schematic view of an experimental apparatus for two-beam interference exposure.

DETAILED DESCRIPTION OF THE INVENTION

The present invention is to be described specifically below.

In the description for a group (atomic group) in the present specification, description with no indication of "substituted or not-substituted" includes those not having substituent and those having substituent. For example, "alkyl group" includes not only an alkyl group not having a substituent (not-substituted alkyl group) but also an alkyl group having a substituent (substituted alkyl group).

(A) Resin which is Decomposed by the Effect of an Acid and Increases the Solubility in an Alkali Developer (Also Referred to as an Acid Decomposable Resin(A))

A resin for use in a chemical amplification type resist membrane for liquid immersion exposure according to the invention is a resin having a monocyclic or polycyclic cycloaliphatic hydrocarbon structure which is decomposed by the effect of an acid and increases the solubility in an alkali developer (acid decomposable resin), and having a group which is decomposed by the effect of an acid to generate an alkali soluble group (hereinafter also referred to as "an acid decomposable group" on the main chain or the side chain of the resin or on both of the main chain and the side chain. The resin of the invention can be preferably used, in particular, for an ArF liquid immersion exposure.

The alkali soluble group includes, for example, a carboxyl group, a hydroxyl group, and a sulfonic group.

a preferred group decomposable with an acid includes, for example, a group in which a hydrogen atom of a —COOH group is substituted with a group which is split with the acid.

The acid decomposable group preferably includes, for example, a cumyl ester group, an enol ester group, an acetal ester group and a tertiary alkyl ester group, with the tertiary alkyl ester group being further preferred.

The resin contained in the positive type resist composition for use in liquid immersion exposure of the invention is preferably a resin having a group represented by the following general formula (I) as the group which is decomposed by the effect of an acid to generate an alkali soluble group (acid decomposable group):

In the general formula (I),
$R_1$ to $R_3$ each independently represents an alkyl group, a cycloalkyl group, or an alkenyl group. At least two of $R_1$ to $R_3$ may bond with each other to form a ring.

As the alkyl group of $R_1$ to $R_3$, an alkyl group of from 1 to 8 carbon atoms is preferred, and it includes, for example, a methyl group, ethyl group, propyl group, n-butyl group, sec-butyl group, 2-hexyl group, and octyl group.

The cycloalkyl group of $R_1$ to $R_3$ may be a monocyclic or polycyclic, and specifically, it includes, groups having a monocyclo, bicyclo, tricyclo or tetracyclo structure having 5 or more carbon atoms. The number of carbon atoms is preferably from 6 to 30 and particularly preferably, from 7 to 25 carbon atoms.

Preferred cycloalkyl groups of $R_1$ to $R_3$ are, for example, an adamantly group, noradamantyl group, decalin residue, tricyclodecanyl group, tetracyclododecanyl group, norbornyl group, cedrol group, cyclohexyl group, cycloheptyl group, cyclooctyl group, cyclodecanyl group, and cyclododecanyl group. More preferred are an adamantyl group, noradamantyl group, decalin residue, tricyclodecanyl group, tetracyclodecanyl group, norbornyl group, cedrol group, cyclohexyl group, cycloheptyl group, cyclooctyl group, cyclodecanyl group and cyclododecanyl group. A portion of a hydrocarbon in the cycloalkyl group may be substituted with a hetero atom such as an oxygen atom.

Preferred alkenyl group of $R_1$ to $R_3$, an alkenyl group of from 2 to 8 carbon atoms and includes, for example, a vinyl group, allyl group, butenyl group, and cyclohexenyl group.

The alkyl group, cycloalkyl group and alkenyl group of $R_1$ to $R_3$ may have a substituent. The substituent includes, for example, an alkyl group, halogen atom, hydroxyl group, alkoxy group, carboxyl group, alkoxycarbonyl group, cyano group, and ester group. As the alkyl group, a lower alkyl group such as a methyl group, ethyl group, propyl group, isopropyl group and butyl group are preferred, and more preferably a methyl group, ethyl group, propyl group and isopropyl group. The alkoxyl group includes, for example, those having from 1 to 4 carbon atoms such as a methoxy group, ethoxy group, propoxy group, and butoxy group. The alkyl group and the alkoxy group may further have a substituent. The substituent which may be present in the alkyl group and the alkoxyl group includes, for example, a hydroxyl group, halogen atom, and alkoxy group.

At least two of $R_1$ to $R_3$ may be bonded with each other to form a ring, in which they may be bonded by way of a hetero atom such as an oxygen atom.

The repetitive unit having the group represented by the general formula (I) may be any repetitive unit, and a repetitive unit represented by the following general formula (pA) is preferred.

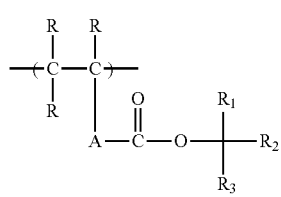

(pA)

In the general formula (pA), R represents a hydrogen atom, a halogen atom or an alkyl group having from 1 to 4 carbon atoms. Plural R may be identical with or different from each other.

A represents a group selected from a single bond, alkylene group, ether group, thioether group, carbonyl group, ester group, amide group, sulfoneamide group, urethane group and urea group, alone or in combination of two or more of them. The alkylene group may have a substituent.

$R_1$ to $R_3$ have the same meanings as those for $R_1$ to $R_3$ defined in the general formula (I).

The repetitive unit represented by the general formula (pA) is, most preferably, a repetitive unit derived from 2-alkyl-2-adamantyl(meth)acrylate or dialkyl(1-adamantyl)methyl (meth)acrylate.

Specific examples of the repetitive unit represented by the general formula (pA) is shown below.

(where Rx represents H, $CH_3$ or $CF_3$.)

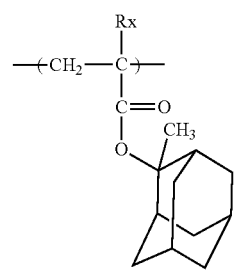

1

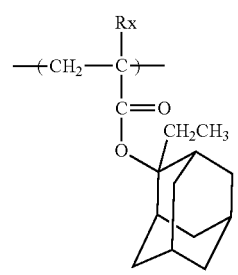

2

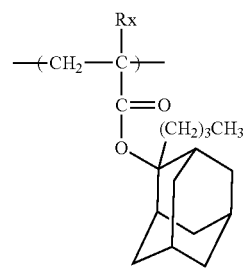

3

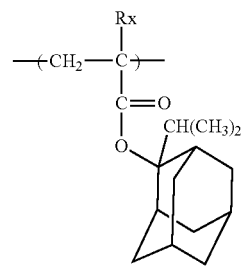

4

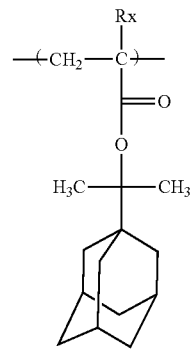

5

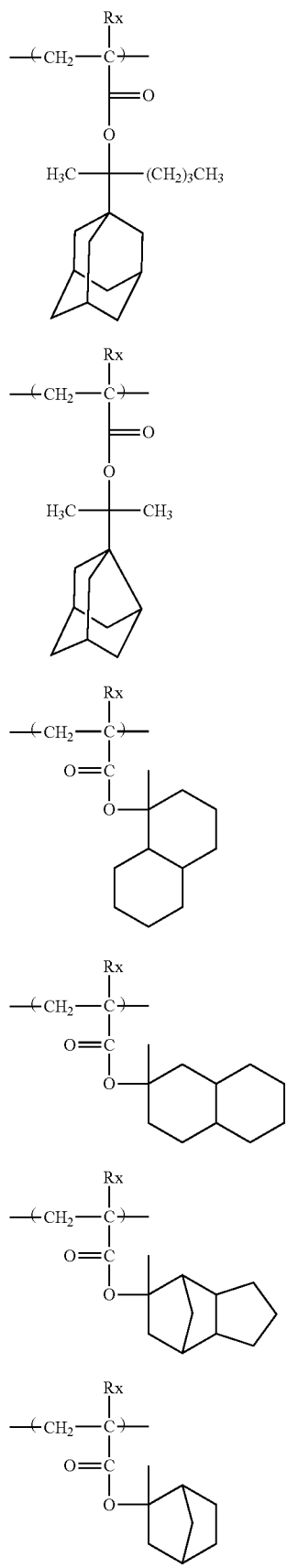
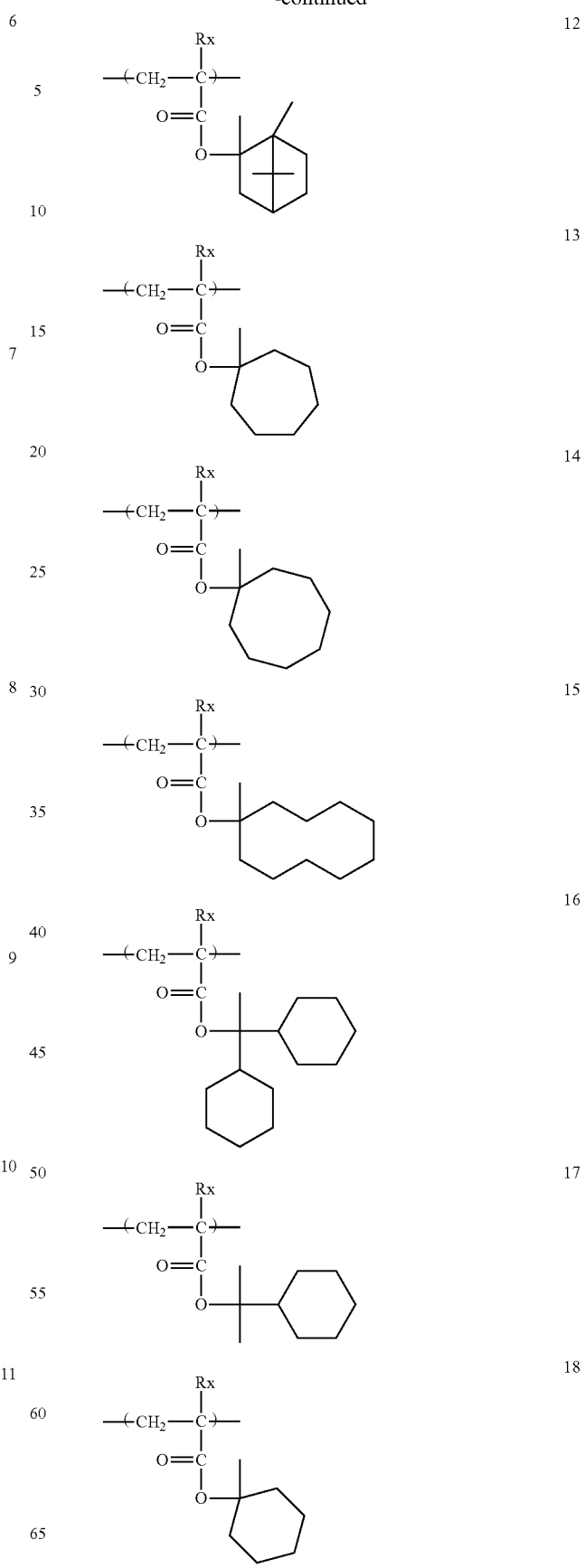

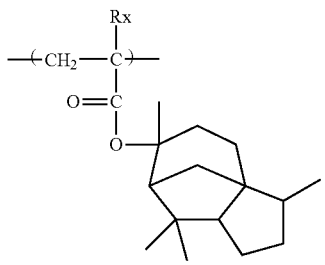

19

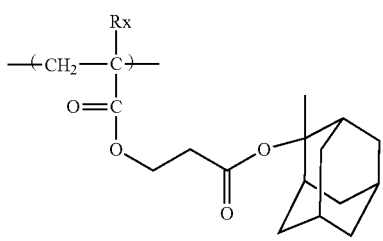

20

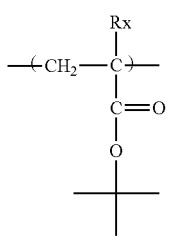

21

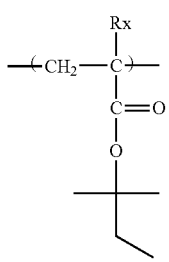

22

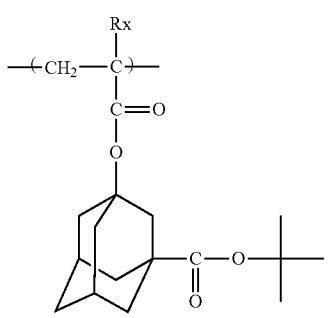

23

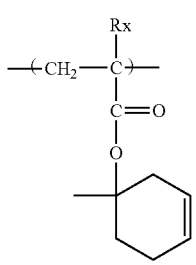

24

In the acid decomposable resin (A), the content of the repetitive group having the group represented by the general formula (I) is preferably, from 10 to 60 mol %, more preferably, from 1 to 50 mol % in the total repetitive units.

The acid decomposable resin (A) may have only the group represented by the general formula (I) as the acid decomposable group, or may have any other acid decomposable group in combination.

The other acid decomposable group which may be present in the decomposable resin (A) includes, for example, —O—C($R_{36}$)($R_{37}$)($R_{38}$), —O—C($R_{36}$)($R_{37}$)(O$R_{39}$), —O—C(=O)—O—C($R_{36}$)($R_{37}$)($R_{38}$), —O—C($R_{01}$)($R_{02}$)(O$R_{39}$), —O—C($R_{01}$)($R_{02}$)—C(=O)—O—C($R_{36}$)($R_{37}$)($R_{38}$).

In the formula, $R_{36}$ to $R_{39}$ each independently represents an alkyl group, a cycloalkyl group, aryl group, aralkyl group or alkenyl group. $R_{36}$ and $R_{37}$, and $R_{38}$ and $R_{39}$ may be bonded with each other to form a ring.

$R_{01}$ and $R_{02}$ each independently represents a hydrogen atom, an alkyl group, cycloalkyl group, aryl group, aralkyl group or alkenyl group.

—C($R_{36}$)($R_{37}$)($R_{38}$) represents a group in which each group represented by $R_{36}$ to $R_{38}$ is bonded to a carbon atom by way of a single bond, here and hereinafter.

For the acid decomposable resin (A), the total amount of the repetitive units having an acid decomposable group including a repetitive unit having an acid decomposable group represented by the general formula (I), as well as a repetitive unit having any other acid decomposable group is preferably from 10 to 70 mol %, more preferably, from 20 to 65 mol %, further more preferably from 25 to 50 mol % based on the total repetitive units.

The monocyclic or polycyclic cycloaliphatic hydrocarbon structure contained in the acid decomposable resin (A) includes, although not particularly restricted, a cycloalkyl group as $R_1$ to $R_3$ in the formula (I) described above and a cycloaliphatic hydrocarbon structure present in the repetitive unit to be described below.

The acid decomposable resin (A) preferably has at least one unit, as the repetitive unit having a monocyclic or polycyclic cycloaliphatic hydrocarbon structure, selected from the group consisting of repetitive units having a partial structure containing a cycloaliphatic hydrocarbon represented by the following general formula (pI) to the general formula (pVI) and repetitive units represented by the following general formula (II-AB).

At first, the partial structure containing a cycloaliphatic hydrocarbon represented by the general formula (pI) to the general formula (pVI) is to be described.

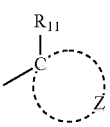

(pI)

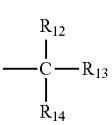

(pII)

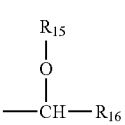

(pIII)

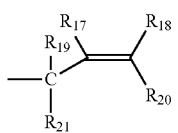 (pIV)

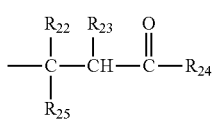 (pV)

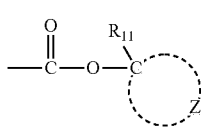 (pVI)

In the formula, $R_{11}$ represents a methyl group, ethyl group, n-propyl group, isopropyl group, n-butyl group, isobutyl group or sec-butyl group, and Z represents an atomic group necessary for forming a cycloaliphatic hydrocarbon group together with a carbon atom.

$R_{12}$ to $R_{16}$ each independently represents a linear or branched alkyl group of 1 to 4 carbon atoms or a cycloaliphatic hydrocarbon group, providing that at least one of $R_{12}$ to $R_{14}$, or either $R_{15}$ or $R_{16}$ represents a cycloaliphatic group.

$R_{17}$ to $R_{21}$ each independently represents a hydrogen atom, a linear or branched alkyl group of 1 to 4 carbon atoms or a cycloaliphatic hydrocarbon group, providing that at least one of $R_{17}$ to $R_{21}$ represents a cycloaliphatic hydrocarbon group. Further, either $R_{19}$ or $R_{21}$ represents a linear or branched alkyl group of 1 to 4 carbon atoms.

$R_{22}$ to $R_{25}$ each independently represents a hydrogen atom or a linear or branched alkyl group of 1 to 4 carbon atoms or a cycloaliphatic hydrocarbon group, providing that at least one of $R_{22}$ to $R_{25}$ represents a cycloaliphatic group. $R_{22}$ and $R_{24}$ may join with each other to form a ring.

The cycloaliphatic hydrocarbon group for $R_{11}$ to $R_{25}$ or the cycloaliphatic hydrocarbon group which is formed by Z and carbon atoms may be monocyclic or polycyclic. Specifically, it includes groups having a monocyclo, bicyclo, tricyclo, or tetracyclo structure of 5 or more carbon atoms. The number of carbon atoms thereof is preferably from 6 to 30 and, particularly preferably, 7 to 25. The cycloaliphatic hydrocarbon groups may have a substituent.

Preferred cycloaliphatic hydrocarbon group are an adamantly group, noradamantyl group, decalin residue, tricyclodecanyl group, tetracyclododecanyl group, norbornyl group, cedrol group, cyclohexyl group, cycloheptyl group, cyclooctyl group, cyclodecanyl group, and cyclododecanyl group. More preferred are the adamantly group, decalin residue, norbornyl group, cedrol group, cyclohexyl group, cycloheptyl group, cyclooctyl group, cylodecanyl group, and cyclododecanyl group.

The substituent which may be present in the cycloaliphatic hydrocarbon groups described above includes, for example, an alkyl group, halogen atom, hydroxyl group, alkoxy group, carboxyl group, and alkoxycarbonyl group. The alkyl group is preferably, lower alkyl groups such as methyl group, ethyl group, propyl group, isopropyl group, and butyl group and, more preferably, selected from the group consisting of a methyl group, ethyl group, propyl group and isopropyl group. The alkoxyl group includes, for example, those having 1 to 4 carbon atoms such as a methoxy group, ethoxy group, propoxy group, and butoxy group. The substituent which may further be present in the alkyl group, alkoxy group and alkoxycarbonyl group, includes, for example, a hydroxyl group, halogen atom and alkoxy group.

The structure represented by the general formulae (pI) to (pVI) in the resin can be used for the protection of the alkali soluble group. The alkali soluble group include various groups known in the relevant technical field.

Specifically, the alkali soluble group includes, for example, a carboxylic acid group, sulfonic acid group, phenol group and thiol group, and the carboxylic acid group and the sulfonic acid group are preferred.

The alkali soluble group protected by the structure represented by the general formulae (pI) to (pVI) in the resin includes, preferably, a structure in which the hydrogen atom of the carboxyl group is substituted with the structure represented by the general formulae (pI) to (pVI).

Specific examples of the repetitive units having the structure in which the hydrogen atom of the carboxyl group is substituted with the structure represented by the general formulae (pI) to (pVI) include, for example, those identical with the specific examples of the repetitive units represented by the general formula (pA).

It is more preferred that the resin of the ingredient (A) contains the repetitive units having a group represented by the general formula (1A).

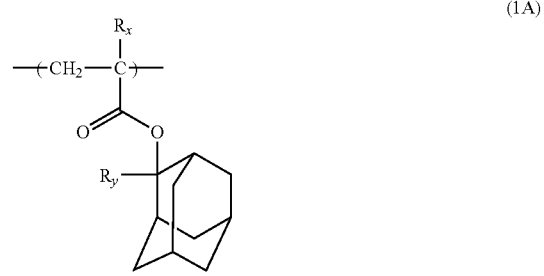 (1A)

In the formula (IA), $R_x$ represents a hydrogen atom or a methyl group.

$R_y$ represents an alkyl group of 1 to 6 carbon atoms. The alkyl group of 1 to 6 carbon atoms in $R_y$ may be linear or branched, and may be not substituted, or may have a further substituent. The substituent which may be present in the alkyl group is, for example, an alkoxy group of 1 to 4 carbon atoms, halogen atom (fluorine atom, chlorine atom, bromine atom, or iodine atom), acyl group, acyloxy group, cyano group, hydroxyl group, carboxyl group, alkoxycarbonyl group, or nitro group.

The repetitive unit represented by the formula (IA) includes repetitive units derived from 2-methyl-2-adamantyl (meth)acrylate, 2-ethyl-2-adamantyl(meth)acrylate, 2-propyl-2-adamantyl(meth)acrylate, 2-isopropyl-2-adamantyl (meth)acrylate, 2-butyl-2-adamantyl(meth)acrylate, and 2-(3-methoxypropyl)-2-adamantyl(meth)acrylate. Preferred are repetitive units derived from 2-methyl-2-adamantyl (meth)acrylate or 2-ethyl-2-adamantyl(meth)acrylate.

Next, the repetitive units having a cycloaliphatic structure represented by the general formula (II-AB) are to be described.

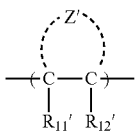

(II-AB)

In the formula (II-AB):

$R_{11}'$ and $R_{12}'$ each independently represents a hydrogen atom, cyano group, halogen atom, or alkyl group.

Z' represents an atomic group containing two bonded carbon atoms (C—C), and for forming a cycloaliphatic structure.

Furthermore, the repetitive unit represented by the general formula (II-AB) is preferably repetitive units represented by the following general formula (II-A) or the general formula (II-B).

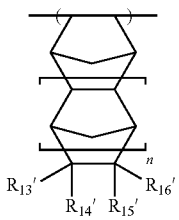

(II-A)

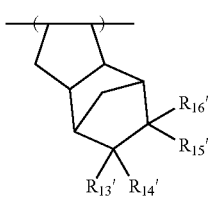

(II-B)

In the formulae (II-A) and (II-B):

$R_{13}'$ to $R_{16}'$ each independently represents a hydrogen atom, halogen atom, hydroxyl group, cyano group, —COOH, —COOR$_5$, a group which is decomposed by the action of an acid, —C(=O)—X-A'-R$_{17}'$, alkyl group or cyclic hydrocarbon group, in which $R_5$ represents an alkyl group, a cyclic hydrocarbon group or the following —Y group.

X represents an oxygen atom, sulfur atom, —NH—, or —NHSO$_2$— or —NHSO$_2$NH—.

A' represents a single bond or a bivalent bonding group.

Further, at least two members of $R_{13}'$ to $R_{16}'$ may join to form a ring. n is 0 or 1.

$R_{17}'$ represents —COOH, —COOR$_5$, —CN, hydroxyl group, alkoxy group, —CO—NH—R$_6$, —CO—NH—SO$_2$—R$_6$ or the following —Y group.

$R_6$ represents an alkyl group or a cyclic hydrocarbon group. —Y group;

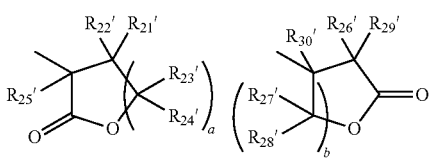

in the —Y group, $R_{21}'$ to $R_{30}'$ each independently represents a hydrogen atom or alkyl group. a and b each presents 1 or 2.

In the general formulae (pI) to (pVI), the alkyl group for $R_{12}$ to $R_{25}$ is a linear or branched alkyl group having 1 to 4 carbon atoms. The alkyl group includes, for example, a methyl group, ethyl group, n-propyl group, isopropyl group, n-butyl group, isobutyl group, sec-butyl group, and t-butyl group.

Furthermore, the substituent which may be present in each of the alkyl groups includes, for example, an alkoxy group of 1 to 4 carbon atoms, halogen atom (fluorine atom, chlorine atom, bromine atom or iodine atom), acyl group, acyloxy group, cyano group, hydroxyl group, carboxy group, alkoxycarbonyl, group and nitro group.

In the general formula (II-AB), $R_{11}'$ and $R_{12}'$ each independently represents a hydrogen atom, cyano group, halogen atom or alkyl group.

Z' represents an atomic group containing two bonded carbon atoms (C—C), and for forming a cycloaliphatic structure.

The halogen atom in the $R_{11}'$ and $R_{12}'$ includes, for example, a chlorine atom, bromine atom, fluorine atom, and iodine atom.

The alkyl group for the $R_{11}'$, $R_{12}'$, and $R_{21}'$ to $R_{30}'$ is preferably a linear or branched alkyl group of 1 to 10 carbon atoms, more preferably, linear or branched alkyl group of 1 to 6 carbon atoms, and further preferably, a methyl group, ethyl group, propyl group, isopropyl group, n-butyl group, isobutyl group, sec-butyl group, and t-butyl group.

A further substituent in the alkyl group includes, for example, a hydroxyl group, halogen atom, carboxyl group, alkoxy group, acyl group, cyano group, and acyloxy group. The halogen atom includes, for example, a chlorine atom, bromine atom, fluorine atom, and iodine atom, the alkoxy group includes those having 1 to 4 carbon atoms, for example, a methoxy group, ethoxy group, propoxy group and butoxy group, the acyl group includes, for example, a formyl group and acetyl group, and the acyloxy group includes, for example, an acetoxy group.

The atomic group for forming the cycloaliphatic structure of Z' is an atomic group forming repetitive units of a cycloaliphatic hydrocarbon which may also have a substituent and, among them, an atomic group for forming a bridged cycloaliphatic structure forming repetitive units of the bridged cycloaliphatic is preferred.

Skeletons of the cycloaliphatic hydrocarbon to be formed can include those identical with the cycloaliphatic hydrocarbon group for $R_{11}$ to $R_{25}$ in the general formulae (pI) to (pVI).

The skeleton of the cycloaliphatic hydrocarbon may have a substituent. Such substituent includes $R_{13}'$ to $R_{16}'$ in the general formula (II-A) or (II-B).

Among the repetitive units having the bridged cycloaliphatic hydrocarbon, repetitive units represented by the general formula (II-A) or (II-B) described above are more preferred.

In the repetitive units represented by the general formula (II-AB), the acid decomposable group may be contained in the —C(=O)—X-A'-R$_{17}'$, or may be contained as a substituent present in the cycloaliphatic structure formed by Z'.

The structure of the acid decomposable group is represented by —C(=O)—X$_1$—R$_0$.

In the formula, $R_0$ represents a tertiary alkyl group such as t-butyl group, or t-amyl group, 1-alkoxyethyl group such as isobornyl group, 1-ethoxyethyl group, 1-butoxyethyl group, 1-isobutoxyethyl group, or 1-cyclohexyloxyethyl group, an alkoxymethyl group such as 1-methoxymethyl group or 1-ethoxymethyl group, 3-oxoalkyl group, tetrahydropyranyl group, tetrahydrofuranyl group, trialkyl silyl ester group, 3-oxo cyclohexyl ester group, 2-methyl-2-adamantyl group, or mevalonic lactone residue. $X_1$ is as defined for the X.

The halogen atom for the $R_{13}'$ to $R_{16}'$ is a chlorine atom, bromine atom, fluorine atom or iodine atom.

The alkyl group for the $R_5$, $R_6$ and $R_{13}'$ to $R_{16}'$ is preferably a linear or branched alkyl group of 1 to 10 carbon atoms, more preferably, linear or branched alkyl groups of 1 to 6 carbon atoms, and further preferably, methyl group, ethyl group, propyl group, isopropyl group, n-butyl group, isobutyl group, sec-butyl group, and t-butyl group.

The cyclic hydrocarbon group for $R_5$, $R_6$ and $R_{13}$ to $R_{16}'$ includes, for example, an alkyl group and bridged hydrocarbon, and includes, for example, cyclopropyl group, cyclopentyl group, cyclohexyl group, adamantly group, 2-methyl-2-adamantyl group, norbornyl group, bornyl group, isobornyl group, tricyclodecanyl group, dicyclopentenyl group, norbornane epoxy group, menthyl group, isomentyl group, neomentyl group and tetracyclododecanyl group.

Among $R_{13}'$ to $R_{16}'$, a ring formed by bonding at least two of them includes, for example, rings of 5 to 12 carbon atoms such as cyclopentene, cyclohexene, cycloheptane and cyclooctane.

The alkoxy group for $R_{17}'$ includes, for example, those of 1 to 4 carbon atoms such as methoxy group, ethoxy group, propoxy group and butoxy group.

An additional substituent for the alkyl group, cyclic hydrocarbon group or alkoxy group includes, for example, hydroxyl group, halogen atom, carboxyl group, alkoxy group, acyl group, cyano group, acyloxy group, alkyl group or cyclic hydrocarbon group. The halogen atom includes is chlorine atom, bromine atom, fluorine atom, or iodine atom. The alkoxy group includes those of 1 to 4 carbon atoms such as methoxy group, ethoxy group, propoxy group and butoxy group, and the acyl group includes, for example, formyl group and acetyl group, and the acyloxy group includes, for example, acetoxy group.

The alkyl group and cyclic hydrocarbon group includes those described above.

The bivalent connection group for A' includes, for example, a group selected from the group consisting of alkylene group, ether group, thioether group, carbonyl group, ester group, amide group, sulfoneamide group, urethane group and urea group, or a combination of two or more of them.

Various kinds of substituents for $R_{13}'$ to $R_{16}'$ in the general formula (II-A) or (II-B) may also be a substituent for the atomic group for forming the cycloaliphatic structure or an atomic group Z for forming a bridged cycloaliphatic structure.

Specific examples of the repetitive units represented by the general formula (II-A) or (II-B) include the following units, but the invention is not restricted to those specific examples.

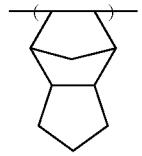

[II-1]

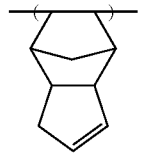

[II-2]

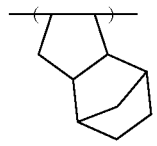

[II-3]

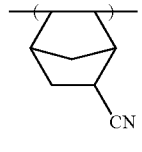

[II-4]

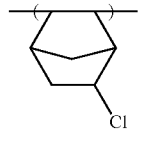

[II-5]

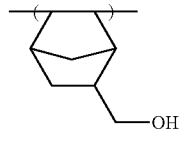

[II-6]

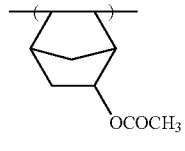

[II-7]

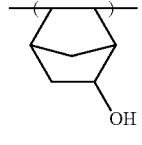

[II-8]

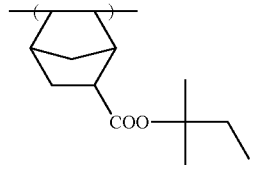

[II-9]

[II-10]

[II-11]

[II-12] 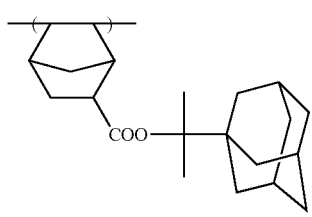
[II-13] 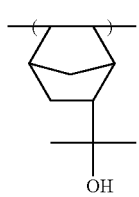
[II-14] 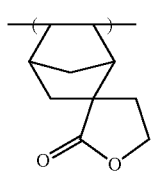
[II-15] 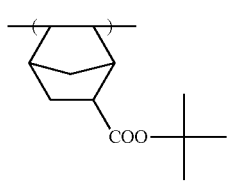
[II-16] 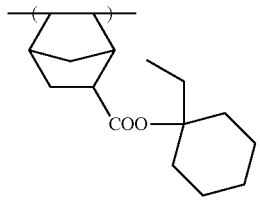
[II-17] 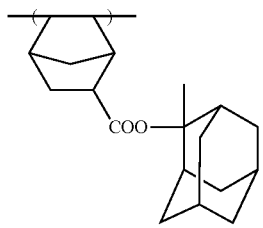
[II-18] 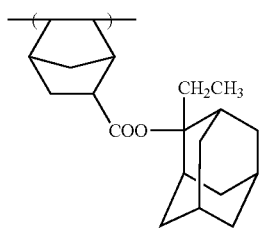
[II-19] 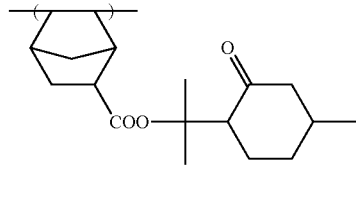
[II-20] 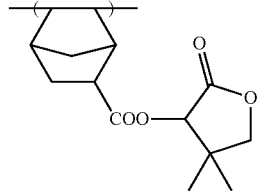
[II-21] 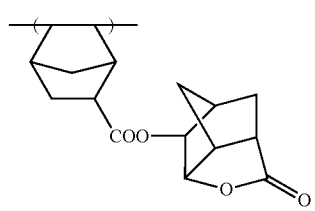
[II-22] 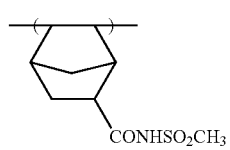
[II-23] 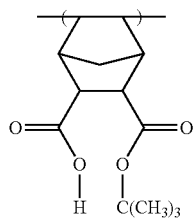
[II-24] 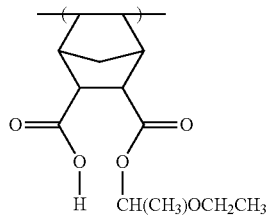
[II-25] 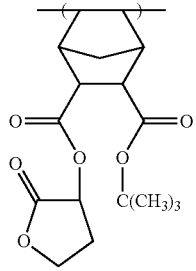

[II-26] 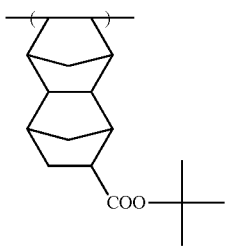

[II-27] 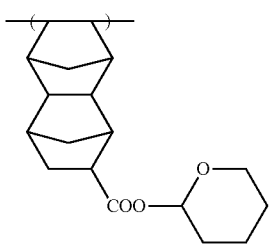

[II-28] 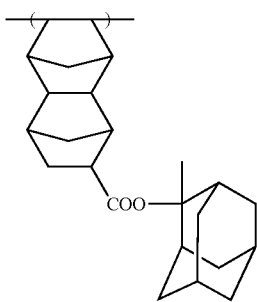

[II-29] 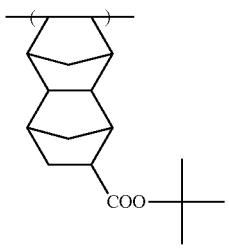

[II-30] 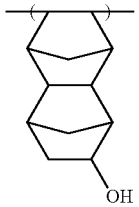

[II-31] 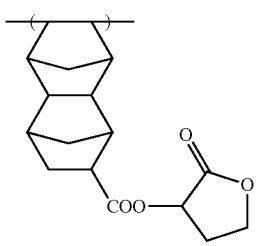

[II-32] 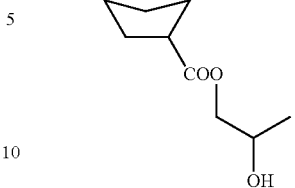

Among the acid decomposable resins (A), the content of repetitive units having a partial structure including the cycloaliphatic hydrocarbons represented by the general formulae (pI) to (pVI) is preferably from 20 to 70 mol %, more preferably, 24 to 65 mol %, and, further, preferably 28 to 60 mol % in the entire repetitive structural units.

In the acid decomposable resin (A), the content of the repetitive units represented by the general formula (II-AB) is preferably from 10 to 60 mol %, more preferably, from 15 to 55 mol % and, further preferably, from 20 to 50 mol % in the entire repetitive structural units.

In the acid decomposable resin (A) having the monocyclic or polycyclic cycloaliphatic hydrocarbon structure, the acid decomposable group represented by the general formula (I) and other decomposing groups may be present in any of the repetitive units having the partial structure containing the cycloaliphatic hydrocarbon represented by the general formula (pI) to general formula (pVI), repetitive units represented by the general formula (II-AB), and repetitive units of other copolymerization ingredients to be described later.

Further, the acid decomposable resin (A) preferably has a lactone group and, more preferably, has repetitive units having a group having a lactone structure represented by the following general formula (Lc) or any one of the following general formulae (III-1) to (III-5), in which the group having the lactone structure may be bonded directly to the main chain.

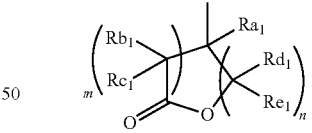
(Lc)

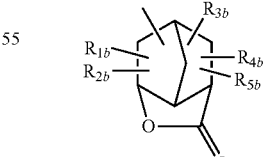
(III-1)

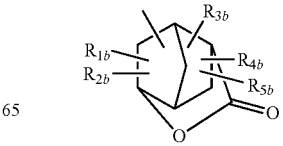
(III-2)

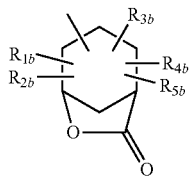
(III-3)

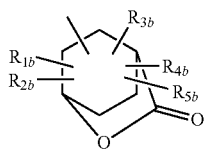
(III-4)

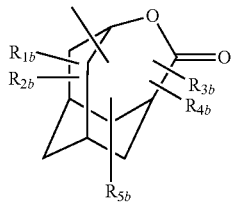
(III-5)

In the general formula (Lc), $Ra_1$, $Rb_1$, $Rc_1$, $Rd_1$, and $Re_1$ each represents hydrogen atom or alkyl group. m and n each independently represents an integer of from 0 to 3, and m+n is 2 or more and 6 or less.

In the general formula (III-1) to (III-5), $R_{1b}$ to $R_{5b}$ each independently represents hydrogen atom, alkyl group, cycloalkyl group, alkoxy group, alkoxycarbonyl group, alkylsulfonylimino group or alkenyl group. Two members of $R_{1b}$ to $R_{5b}$ may join to form a ring.

The alkyl group for $Ra_1$ to $Re_1$ in the general formula (Lc) and the alkyl group for the alkyl group, alkoxy group, alkoxycarbonyl group or alkylsulfonylimino group for $R_{1b}$ to $R_{5b}$ include linear or branched alkyl groups which may have a substituent.

A preferred substituent includes, for example, alkoxy group of 1 to 4 carbon atom, halogen atom (fluorine atom, chlorine atom, bromine atom, or iodine atom), acyl group of 2 to 5 carbon atoms, acyloxy group of 2 to 5 carbon atoms, cyano group, hydroxyl group, carbonyl group, alkoxycarbonyl group of 2 to 5 carbon atoms, and nitro group.

The repetitive unit containing a group having a lactone structure represented by the general formula (Lc) or any one of the general formulae (III-1) to (III-5) includes, for example, those in which at least one of $R_{13}'$ to $R_{16}'$ in the general formula (II-A) or the general formula (II-B) has a group represented by the general formula (III-1) to (III-5) (for example, a group in which $R_5$ in —$COOR_5$ is a group represented by the general formula (Lc) or the general formulae (III-1) to (III-5)), or a repetitive unit represented by the following general formula (AI).

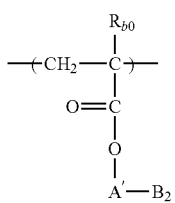
(AI)

In the general formula (AI), $R_{b0}$ represents hydrogen atom, halogen atom or alkyl group of 1 to 4 carbon atoms. A preferred substituent which may be present in the alkyl group for $R_{b0}$ includes those previously exemplified as preferred substituents which may be present in the alkyl group for $R_{1b}$ in the general formulae (III-1) to (III-5).

The halogen atom for $R_{b0}$ is fluorine atom, chlorine atom, bromine atom, or bromine atom. $R_{b0}$ is, preferably, hydrogen atom.

A' represents single bond, ether bond, ester bond, carbonyl group, alkylene group or bivalent group of the combination of them.

$B_2$ represents a group represented by the general formula (Lc) or any one of the general formulae (III-1) to (III-5).

Specific examples of the repetitive unit containing the group having a lactone structure are to be described below, but the invention is not restricted to them.

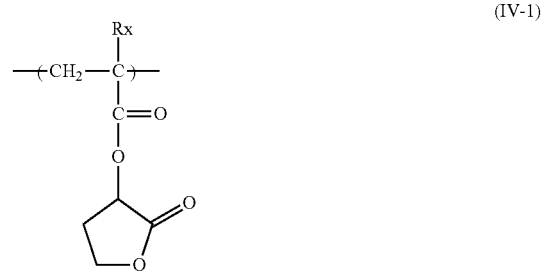
(IV-1)

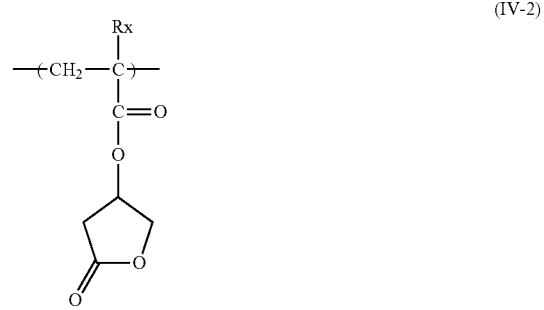
(IV-2)

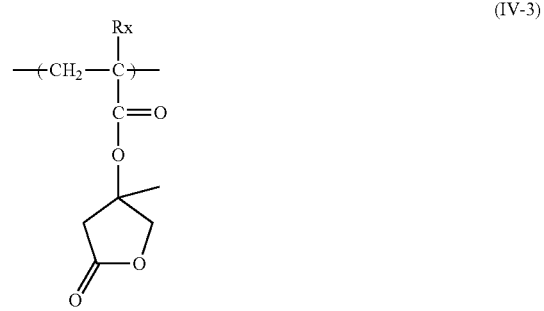
(IV-3)

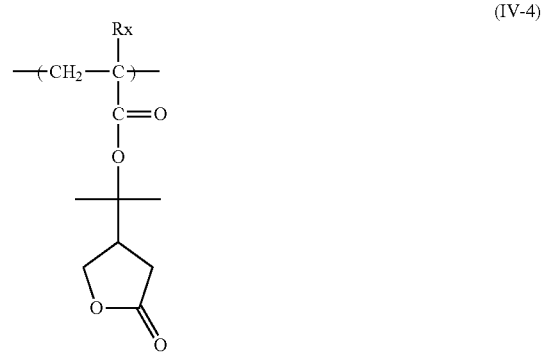
(IV-4)

(IV-5) 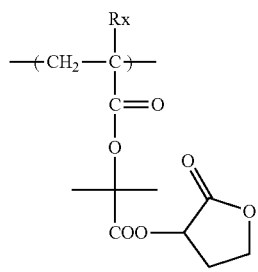
(IV-6) 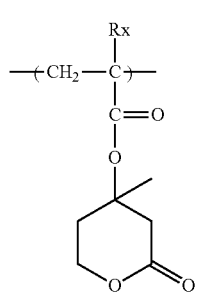
(IV-7) 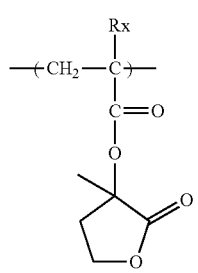
(IV-8) 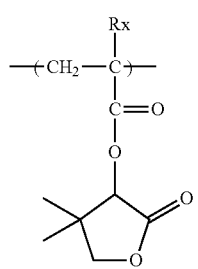
(IV-9) 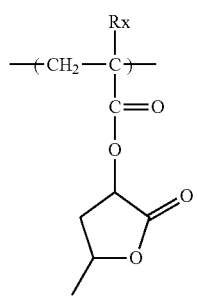
(IV-10) 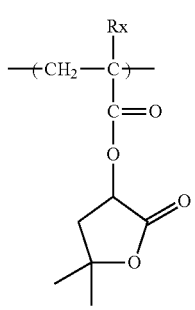
(IV-11) 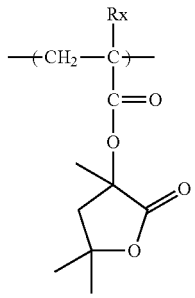
(IV-12) 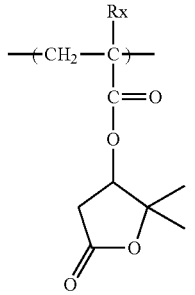
(IV-13) 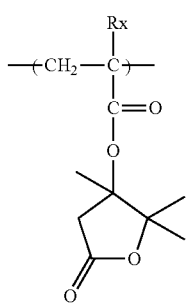
(IV-14) 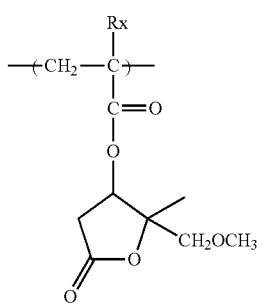
(IV-15) 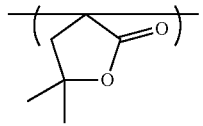

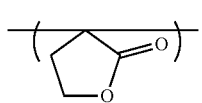
(IV-16)
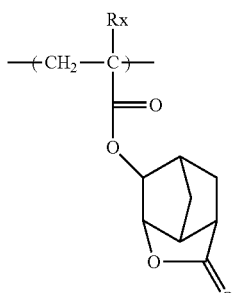
(Ib-1)
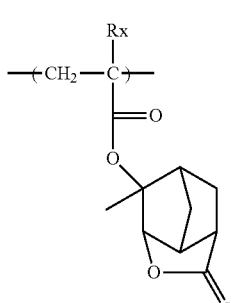
(Ib-2)
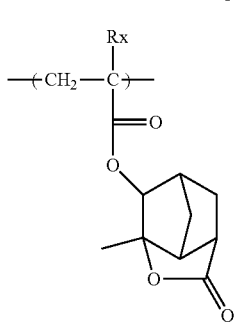
(Ib-3)
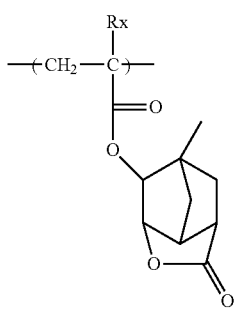
(Ib-4)
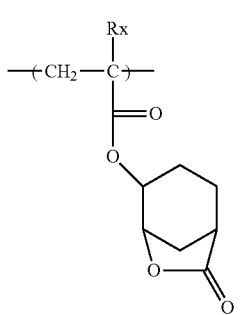
(Ib-5)
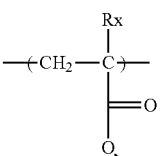
(Ib-6)
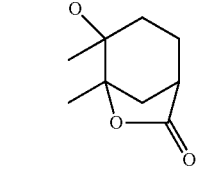
(Ib-7)
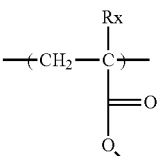
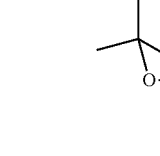
(Ib-8)
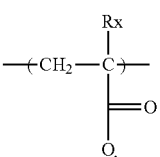
(Ib-9)
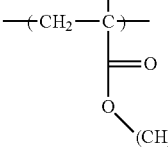
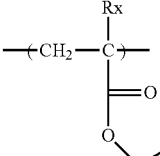
(Ib-10)
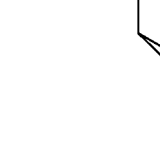

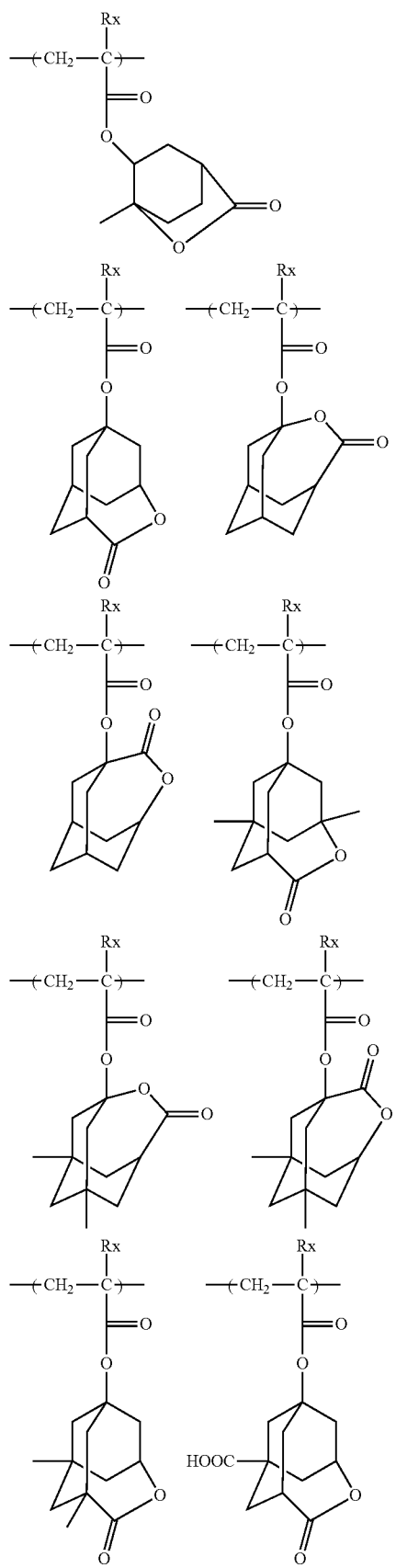

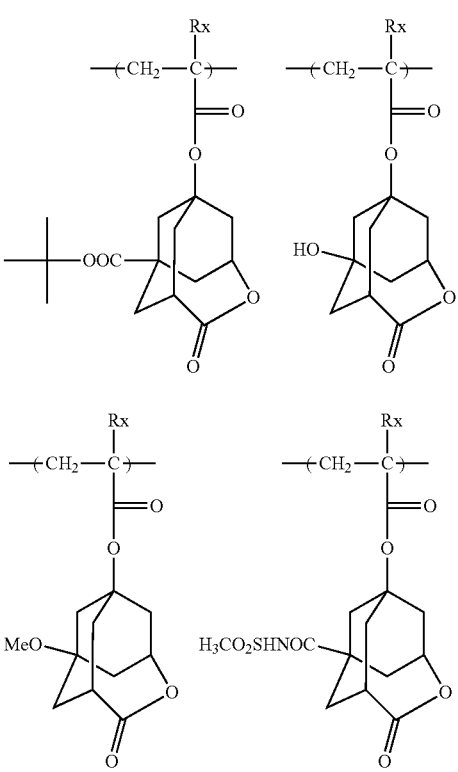

(where Rx represents H, CH₃ or CF₃.)

The acid decomposable resin (A) may contain a repetitive unit having a group represented by the following general formula (IV).

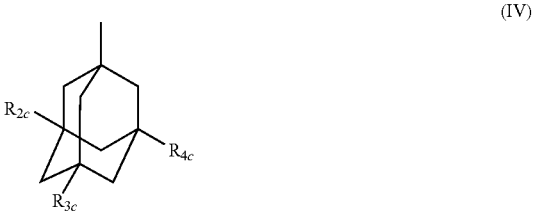

(IV)

In the general formula (IV), $R_{2c}$ to $R_{4c}$ each independently represents hydrogen atom or hydroxyl group, providing that at least one of $R_{2c}$ to $R_{4c}$ represents hydroxyl group.

The group represented by the general formula (IV) is preferably, of a dihydroxy form or monohydroxy form, more preferably, of a dihydroxy form.

The repetitive unit having a group represented by the general formula (IV) includes, for example, those having a group in which at least one of $R_{13}'$ to $R_{16}'$ in the general formula (II-A) or (II-B) has a group represented by the general formula (IV) (for example, $R_5$ in —COOR₅ is a group represented by the general formula (IV)), or repetitive units represented by the following general formula (AII).

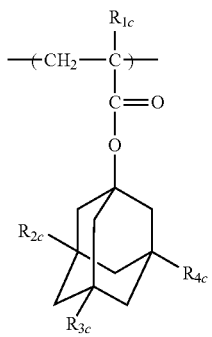
(AII)

In the general formula (AII), $R_{1c}$ represents hydrogen atom or methyl group.

$R_{2c}$ to $R_{4c}$ each independently represents hydrogen atom or hydroxyl group, providing that at least one of $R_{2c}$ to $R_{4c}$ represents hydroxyl group and preferably, two members of $R_{2c}$ to $R_{4c}$ each represents hydroxyl group.

Specific examples of the repetitive unit having the structure represented by the general formula (AII) are shown below, but they are not limited to them.

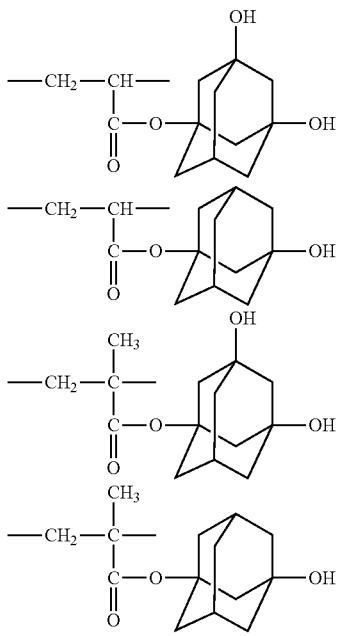

The acid decomposable resin (A) may have a repetitive unit represented by the following general formula (V).

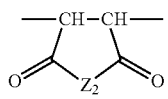
(V)

In the general formula (V), $Z_2$ represents —O— or —N($R_{41}$)—. $R_{41}$ represents hydrogen atom, hydroxyl group, alkyl group or —OSO$_2$—$R_{42}$. $R_{42}$ represents alkyl group, cycloalkyl group or camphor residue. The alkyl group, cycloalkyl group, or camphor residue for $R_{41}$ or $R_{42}$ may be substituted with halogen atom (preferably, fluorine atom).

The repetitive unit represented by the general formula (V) includes those specific examples below, but they are not restricted to them.

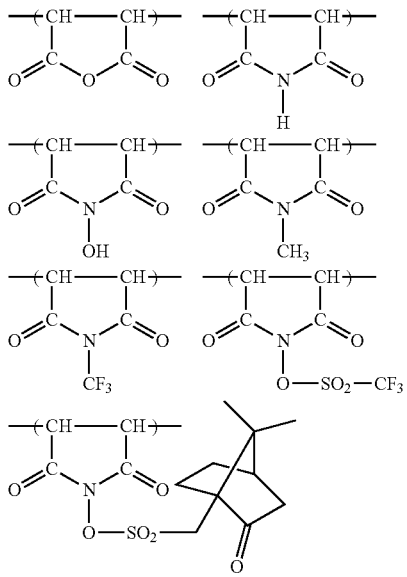

The acid decomposable resin (A) can contain, in addition to the repetitive structural units described above, various repetitive structural units with an aim of controlling the dry etching resistance, standard liquid developer adaptability, substrate adhesion property, resist profile and, further, resolution, heat resistance, sensitivity, etc. which are generally necessary characteristics of the resist.

Such repetitive structural units include the repetitive structural unit corresponding to the following monomers, but they are not restricted to them.

This enables for fine control of the performance required for the resin of the ingredient (A), especially, (1) solubility to a coating solvent,
(2) film-forming property (glass transition point),
(3) alkali developability,
(4) film reduction (selection of hydrophilic/phobic property, alkali solubility group selection),
(5) adhesion to substrate at not exposed area,
(6) dry etching resistance, etc.

Such monomers include compounds having one addition polymerizable unsaturated bond selected, for example, from acrylate esters, methacrylate esters, acrylamides, methacrylamides, allyl compounds, vinyl ethers, and vinyl esters.

In addition, any of addition polymerizable compounds that are copolymerizable with the monomer corresponding to the various repetitive structural units described above also may be copolymerized.

In the acid decomposable resin A, the molar ratio of each of the repetitive structural units contained is properly set so as to control the dry etching resistance or adaptability to standard liquid developer, a substrate adhesion, profile of the resist and, further, resolution, heat resistance, sensitivity, etc. which are general necessary performances of the resist.

While the content of the repetitive structural units based on the monomers of the further copolymerizable ingredients in the resin can also be set appropriately depending on the desired performances of the resist, generally, it is preferably 99 mol % or less, more preferably, 90 mol % or less, further preferably, 80 mol % or less based on the total mol number of the repetitive structural units having a partial structure containing cycloaliphatic hydrocarbon represented by the general formulae (pI) to (pVI) and the repetitive units represented by the general formula (II-AB).

The content especially of the repetitive units containing a group having the lactone structure described above and the repetitive units containing the group represented by the general formula (IV) (hydroxyadamantane structure) is as follows.

Based on the summed total mol number of the repetitive structural units having a partial structure containing the cycloaliphatic hydrocarbon represented by the general formulae (pI) to (pVI) and the repetitive units represented by the general formula (II-AB), the content of the repetitive units containing a group having the lactone structure is preferably from 1 to 70 mol %, more preferably, from 10 to 70 mol %, and the content of the repetitive units containing the group represented by the general formula (IV) is preferably, from 1 to 70 mol %, more preferably, from 1 to 50 mol %.

In a case where the composition of the invention is for exposure to ArF, it is preferred that the resin has no aromatic group in view of transparency to ArF light.

The acid decomposable resin (A) can be synthesized by ordinary method (for example, radical polymerization).

For example, the general synthesis method comprises charging monomer species into a reaction vessel collectively or in the course of the reaction, dissolving them, for example, in ethers such as tetrahydrofuran, 1,4-dioxane, and diisopropyl ether, ketones such as methyl ethyl ketone, and methyl isobutyl ketone, ester solvents such as ethyl acetate and further, in a solvent that dissolves the composition of the invention such as propylene glycol monomethyl ether acetate to be described later, making them uniform, then optionally carrying out heating in an inert gas atmosphere such as of nitrogen or argon and starting polymerization by using a commercially available radical initiator (such as azo type initiator, peroxides, etc.). If required, an initiator is add or added divisionally and, after completing the reaction, the reaction product is charged into a solvent and the desired polymer is recovered by a method such as in the form of power or solid. The concentration in the reaction is usually 20 mass % or more, preferably, 30 mass % or more, further preferably, 40 mass % or more. The temperature for the reaction is usually from 10° C. to 150° C., preferably, from 30° C. to 120° C., further preferably, from 50 to 100° C.

The repetitive structural units may be used each alone, or may be used as a combination of a plurality of them. In addition, the resin may be used alone, or may be used as a combination of a plurality of them.

The weight average molecular weight of the acid decomposable resin (A), on the basis of polystyrene by a gas permeation chromatography (GPC) method, is preferably from 1,000 to 200,000, more preferably, from 3,000 to 20,000. By determining the weight average molecular weight to 1,000 or more, heat resistance and dry etching resistance can be improved, and by determining the weight average molecular weight to 200,000 or less, the developing property can be improved, and in addition, the viscosity is lowered to result in improvement of the film-forming property.

Referring to the molecular weight distribution (Mw/Mn, also referred to as dispersibility), those in a range usually, from 1 to 5, preferably, from 1 to 4, further preferably, from 1 to 3 are used. The molecular weight distribution is preferably 5 or less in view of the resolution, configuration of the resist, side wall of the resist pattern and roughness.

The amount of residual monomers in the acid decomposable monomer (A) is preferably, from 0 to 10 mass %, more preferably, from 0 to 5 mass %.

In the positive type resist composition of the invention, the blending amount of the acid decomposable resin (A) is, preferably, from 40 to 99.99 mass %, more preferably, from 50 to 99.97 mass % based on the total solid content of the resist.

(B) Compound Generating Acid Upon Irradiation with One of an Actinic Ray and a Radiation The compound that generates acid upon irradiation with one of an actinic ray and a radiation to be used for the positive type resist composition for use in immersion exposure according to the invention (hereinafter sometimes referred to as "acid generator") is to be described below.

The acid generator used in the invention can be selected from the compounds used generally as the acid generator.

That is, photoinitiator for photo-cationic polymerization, photoinitiator for photo-radical polymerization, light extinguishing agent for dyes, light discolorant, or known compounds that generate acid upon irradiation with one of an actinic ray and a radiation such as far UV-rays and X-rays used for microresist or the like, as well as mixtures thereof can be properly selected and used.

They include, for example, diazonium salt, phosphonium salt, sulfonium salt, iodonium salt, imidosulfonate, oximesulfonate, diazodisulfone, disulfone and o-nitrobenzylsulfonate.

For compounds in which the group or the compound generating an acid upon irradiation with one of an actinic ray and a radiation are introduced to the main chain or the side chains of the polymer, for example, compounds described in U.S. Pat. No. 3,849,137, GP No. 3914407, JP-A Nos. 63-26653, 55-164824, 62-69263, 63-146038, 63-163452, 62-153853, and 63-146029 can be used.

In addition, compounds generating an acid by light described in U.S. Pat. No. 3,779,778 and EP No. 126,712 can also be used.

Preferred compounds, among the acid generating agents, include compounds represented by the following general formulae (ZI), (ZII) and (ZIII).

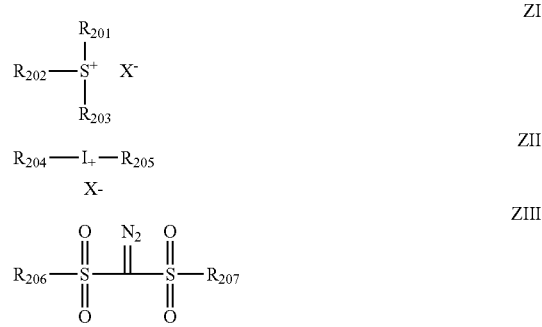

In the general formula (ZI), $R_{201}$, $R_{202}$ and $R_{203}$ each independently represents an organic group.

$X^-$ represents a non-nucleophilic anion.

The number of carbon atoms in the organic group as $R_{201}$, $R_{202}$ or $R_{203}$ is generally from 1 to 30, preferably, from 1 to 20.

Two members of $R_{201}$ to $R_{203}$ may join to form a ring structure, and the ring may have an oxygen atom, sulfur atom, ester bond, amide bond, or carbonyl group therein.

As the group formed by joining two members of $R_{201}$ to $R_{203}$ includes an alkylene group (for example, butylene group or pentylene group).

Specific examples of the organic group as $R_{201}$, $R_{202}$, and $R_{203}$ include, for example, groups corresponding to those in the compounds (Z1-1), (Z1-2), and (Z1-3) to be described later.

Compounds having a plurality of structures represented by the general formula (ZI) may also be adopted. For example, compounds having such a structure that at least one of $R_{201}$ to $R_{203}$ of the compounds represented by the general formula (ZI) joins with at least one of $R_{201}$ to $R_{203}$ of other compounds represented by the general formula (ZI).

Further preferred (ZI) ingredients include compounds (Z1-1), (Z1-2), and (Z1-3) to be described below.

The compound (Z1-1) is an arylsulfonium compound in which at least one of $R_{201}$ to $R_{203}$ of the general formula (ZI) is an aryl group, that is, a compound having arylsulfonium as a cation.

In the arylsulfonium compound, all of $R_{201}$ to $R_{203}$ may be an aryl group, and a portion of $R_{201}$ to $R_{203}$ may be an aryl group, and the residues may be an aryl group and a cycloalkyl group.

The arylsuofonium compound includes, for example, triarylsulfonium compounds, diaryalkyl sulfonium compounds, aryldialkyl sulfonium compounds, diarylcycloalkyl sulfonium compounds, and aryldicycloalkyl sulfonium compounds.

The aryl group of the arylsulfonium compound is, preferably, a phenyl group and a naphthyl group and more preferably, a phenyl group. In a case where the arylsulfonium compound has two or more aryl groups, the two or more aryl groups may be identical with or different from each other.

The alkyl group which is optionally present in the arylsulfonium compound is preferably a linear or branched alkyl group of from 1 to 15 carbon atoms and includes, for example, a methyl group, ethyl group, propyl group, n-butyl group, sec-butyl group or t-butyl group.

The cycloalkyl group which is optionally present in the arylsulfonium compound is, preferably, a cycloalkyl group of from 3 to 15 carbon atoms and includes, for example, a cyclopropyl group, cyclobutyl group is cyclohexyl group.

The aryl group, alkyl group, or cycloalkyl group for $R_{201}$ to $R_{203}$ may have an alkyl group (for example, of 1 to 15 carbon atoms), cycloalkyl group (for example, of 3 to 15 carbon atoms), aryl group (for example, of 6 to 14 carbon atoms), alkoxy group (for example, 1 to 15 carbon atoms), halogen atom, hydroxyl group or phenylthio group as a substituent. The substituent includes, preferably, a linear or branched alkyl group of 1 to 12 carbon atoms, cycloalkyl group of 3 to 12 carbon atoms, alkoxy group of 1 to 12 carbon atom, and, most preferably, an alkyl group of 1 to 4 carbon atoms, and alkoxy group of 1 to 4 carbon atoms. The substituent may be substituted on any one of three members of $R_{201}$ to $R_{203}$, and may be substituted on all of the three members. In a case where $R_{201}$ to $R_{203}$ each represents an aryl group, the substituent is preferably at the p-position of the aryl group.

The non-nucleophilic anion as $X^-$ includes, for example, a sulfonic acid anion, carboxylic acid anion, sulfonylimide anion, bis(alkylsulfonyl)imide anion, and tris(alkylsulfonyl) methyl anion.

The non-nucleophilic anion means an anion with extremely low effect of causing nucleophilic reaction, which is an anion capable of suppressing aging decomposition by intra-molecular nucleophilic reaction.

The sulfonic acid anion includes, for example, an aliphatic sulfonic acid anion, aromatic sulfonic acid anion, or camphor sulfonic acid anion.

The carboxylic acid anion includes, for example, an aliphatic carboxylic acid anion, aromatic carboxylic acid anion, and aralkyl carboxylic acid anion.

The aliphatic group in the aliphatic sulfonic acid anion includes, for example, an alkyl group of 1 to 3 carbon atoms, specifically, a methyl group, ethyl group, propyl group, isopropyl group, n-butyl group, isobutyl group, sec-butyl group, pentyl group, neopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group and a cycloalkyl group of 3 from 30 carbon atoms, specifically, a cyclopropyl group, cyclopentyl group, cyclohexyl group, adamantyl group, norbornyl group, and boronyl group.

The aromatic group in the aromatic sulfonic acid anion include, preferably, aryl group of 6 to 14 carbon atoms, for example, a phenyl group, tolyl group, and naphthyl group.

The alkyl group, cycloalkyl group and aryl group in the aliphatic sulfonic acid anion and aromatic sulfonic acid anion may have a substituent.

Such substituent include, for example, a nitro group, halogen atom (fluorine atom, chlorine atom, bromine atom, or iodine atom), carboxyl group, hydroxyl group, amino group, cyano group, alkoxy group (preferably of 1 to 5 carbon atoms), cycloalkyl group (preferably of 3 to 15 carbon atoms), aryl group (preferably of 6 to 14 carbon atoms), alkoxycarbonyl group (preferably of 2 to 7 carbon atoms), acyl group (preferably of 2 to 12 carbon atoms), alkoxycarbonyl oxy group (preferably of 2 to 7 carbon atoms), and alkylthio group (preferably of 1 to 15 carbon atoms). The aryl group and the ring structure which are present in each group may further include alkyl group preferably of 1 to 15 carbon atoms as a substituent.

The aliphatic group in the aliphatic carboxylic acid anion includes those identical with the aliphatic group in the aliphatic sulfonic acid anion.

The aromatic group in the aromatic carboxylic acid anion includes those identical with the aromatic group in the aromatic sulfonic acid anion.

The aralkyl group in the aralkyl carboxylic acid anion includes preferably an aralkyl group of 6 to 12 carbon atoms, for example, benzyl group, phenetyl group, naphthyl methyl group, naphthyl ethyl group, and naphthyl methyl group.

The aliphatic group, aromatic group, and aralkyl group in the aliphatic carboxylic acid anion, aromatic carboxylic acid anion, and aralkyl carboxylic acid anion may have a substituent, and the substituent includes, for example, a halogen atom, alkyl group, cycloalkyl group, alkoxy group, and alkyl thio group, like those for the aliphatic sulfonic acid anion.

The sulfonylimide anion includes, for example, a saccharin anion.

The alkyl group in the bis(alkylsulfonyl)imide anion, and tris(alkylsulfonyl)methyl anion is preferably an alkyl group of 1 to 5 carbon atoms and includes, for example, methyl group, ethyl group, propyl group, isopropyl group, n-butyl group, isobutyl group, sec-butyl group, pentyl group, and neopentyl group. Those alkyl groups may have a substituent, and the substituent includes, a halogen atom, and alkyl group, alkoxy group, and alkylthio group substituted with a halogen atom, and the alkyl group substituted with a fluorine atom is preferred.

Other non-nucleophilic anions include, for example, phosphorous fluoride, boron fluoride, and antimony fluoride.

The non-nucleophilic anion for $X^-$ is preferably an aliphatic sulfonic acid anion substituted at α-position of sulfonic acid with a fluorine atom, an aromatic sulfonic acid anion substituted with a fluorine atom or a group having a fluorine atom, a bis(alkyl sulfonyl)imide anion in which the alkyl group is substituted with a fluorine atom, and a tris (alkylsulfonyl)methide anion in which the alkyl group is substituted with a fluorine atom. The non-nucleophilic anion is, particularly preferably, a perfluoro aliphatic sulfonic acid anion of 4 to 8 carbon atoms, and an aromatic sulfonic anion having a fluorine atom and, more preferably, nonafluorobutane sulfonic acid anion, perfluorooctane sulfonic acid anion, pentafluorobenzene sulfonic acid anion, and 3,5-bis(trifluoromethyl)benzene sulfonic acid anion.

Then, the compound (Z1-2) is to be described.

The compound (Z1-2) is a compound in a case where $R_{201}$ to $R_{203}$ in the general formula (ZI) each independently represents an organic group containing no aromatic ring. In this case, the aromatic ring also includes aromatic rings containing hetero atoms.

The organic group containing no aromatic ring as $R_{201}$ to $R_{203}$ has generally 1 to 30 carbon atoms, preferably, 1 to 20 carbon atoms.

$R_{201}$ to $R_{203}$ each independently represents, preferably, an alkyl group, cycloalkyl group, allyl group, or vinyl group, further preferably, a linear, branched, cyclic 2-oxoalkyl group, or alkoxycarbonyl methyl group and, most preferably, the linear or branched 2-oxoalkyl group.

The alkyl group as $R_{201}$ to $R_{203}$ may be either linear or branched, and preferably includes a branched alkyl group of 1 to 10 carbon atoms, for example, a methyl group, ethyl group, propyl group, butyl group, or pentyl group. The alkyl group is, more preferably, a 2-linear or branched oxoalkyl group, or alkoxycarbonyl methyl group.

The cycloalkyl group as $R_{201}$ to $R_{203}$ is preferably a cycloalkyl group of 3 to 10 carbon atoms and includes, for example, a cyclopentyl group, cyclohexyl group, or norbornyl group. The cycloalkyl group is, more preferably, 2-oxocycloalkyl group.

The 2-oxoalkyl group may be any of linear, branched and cyclic, and includes preferably, a group having >C=O at the 2-position of the alkyl group or cycloalkyl group.

The alkoxy group in the alkoxycarbonyl methyl group preferably includes alkyl groups of 1 to 5 carbon atoms (methyl group, ethyl group, propyl group, butyl group, and pentyl group).

$R_{201}$ to $R_{203}$ may be substituted with a halogen atom, alkoxy group (for example, of 1 to 5 carbon atoms), hydroxyl group, cyano group or nitro group).

Two of $R_{201}$ to $R_{203}$ may join to form a ring structure, and may have an oxygen atom, sulfur atom, ester bond, amide bond, or carbonyl group in the ring. The group formed by joining two member of $R_{201}$ to $R_{203}$ includes an alkylene group (for example, butylenes group and pentylene group).

The compound (Z1-3) is a compound represented by the following general formula (Z1-3), which is a compound having a phenacyl sulfonium salt structure.

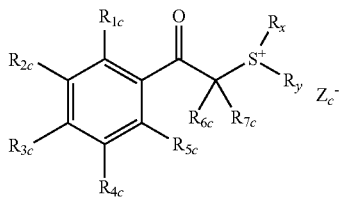

(Z1-3)

$R_{1c}$ to $R_{5c}$ each independently represents a hydrogen atom, alkyl group, cycloalkyl group, alkoxy group or halogen atom.

$R_{6c}$ and $R_{7c}$ each represents a hydrogen atom, alkyl group or cycloalkyl group.

$R_x$ and $R_y$ each independently represents an alkyl group, cycloalkyl group, allyl group or vinyl group.

Any two or more of $R_{1c}$ to $R_{5c}$, and $R_x$ and $R_y$ may join to form a ring structure respectively, and the ring structure may have an oxygen atom, sulfur atom, ester bond, or amide bond.

$Zc^-$ represents a non-nucleophilic anion, and includes those identical with the non-nucleophilic anion of $X^-$ in the general formula (ZI).

The alkyl group as $R_{1c}$ and $R_{5c}$ is preferably a linear or branched alkyl group of 1 to 20 carbon atoms, for example, a methyl group, ethyl group, linear or branched propyl group, linear or branched butyl group, or linear or branched pentyl group.

The cycloalkyl group as $R_{1c}$ and $R_{7c}$ is preferably a cycloalkyl group of 3 to 8 carbon atoms, for example, a cyclopentyl group, or cyclohexyl group.

The alkoxy group as $R_{1c}$ and $R_{7c}$ may be any of linear, branched or cyclic, and includes, for example, an alkoxy group of 1 to 10 carbon atoms, and preferably, a linear or branched alkoxy group of 1 to 5 carbon atoms (for example, methoxy group, ethoxy group, linear or branched propoxy group, linear or branched butoxy group, or linear or branched pentoxy group), a cyclic alkoxy group of 3 to 8 carbon atoms (for example, cyclopentyloxy group, and cyclohexyloxy group).

Preferably, any one of $R_{1c}$ and $R_{5c}$ is linear or branched alkyl group, cycloalkyl group or linear, branched or cyclic alkoxy group, and further preferably, the sum of the number of carbon atoms in $R_{1c}$ to $R_{5c}$ is 2 to 15. This can improve the solvent-solubility and suppress generation of particles during storage.

The alkyl group and cycloalkyl group as $R_x$ and $R_y$ are the same as the alkyl group and cycloalkyl group for $R_{1c}$ to $R_{7c}$, and 2-oxoalkyl group, 2-oxocycloalkyl group and alkoxycarbonyl methyl group are more preferred.

The 2-oxoalkyl group and 2-oxocycloalkyl group include those having >C=O at the 2-position of the alkyl group and cycloalkyl group as $R_{1c}$ to $R_{7c}$.

The alkoxy group in the alkoxycarbonyl methyl group includes those identical with alkoxy groups as $R_{1c}$ to $R_{5c}$.

The group formed by joining $R_x$ and $R_y$ includes a butylenes group, pentylene group, etc.

$R_x$ and $R_y$ each represents, preferably, an alkyl group of 4 or more carbon atoms, more preferably, an alkyl group of 6 or more carbon atoms, further preferably, an alkyl group of 8 or more carbon atoms.

In the general formulae (ZII) and (ZIII), $R_{204}$ to $R_{207}$ each independently represents an aryl group, alkyl group, or cycloalkyl group.

The aryl group as $R_{204}$ to $R_{207}$ includes, preferably, a phenyl group and naphthyl group, further preferably, a phenyl group.

The alkyl group as $R_{204}$ to $R_{207}$ includes, preferably, linear or branched alkyl group of 1 to 10 carbon atoms, for example, a methyl group, ethyl group, propyl group, butyl group, and pentyl group.

The cycloalkyl group as $R_{204}$ to $R_{207}$ includes cycloalkyl groups of 3 to 10 carbon atoms, for example, cyclopentyl group, cyclohexyl group, and norbornyl group.

The substituent which can be present in $R_{204}$ to $R_{207}$ includes, for example, alkyl groups (of, for example, 1 to 15 carbon atoms), cycloalkyl groups (of, for example, 3 to 15 carbon atoms), aryl groups (of, for example, 6 to 15 carbon atoms), alkoxy groups (of, for example, 1 to 15 carbon atoms), and halogen atom, hydroxyl group, and phenylthio group.

$X^-$ represents a non-nucleophilic anion, and includes those identical with the non-nucleophilic anion as $X^-$ in the general formula (ZI).

Preferred compound as the acid generator further includes compounds represented by the following general formulae (ZIV), (ZV), and (ZVI).

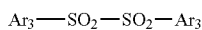

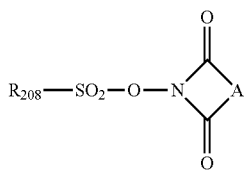

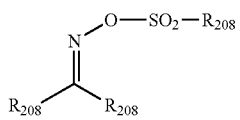

In the general formula (ZIV), two $Ar_3$ each independently represents an aryl group.

$R_{208}$ in the general formulae (ZV) and (ZVI) each independently represents an alkyl group, cycloalkyl group or aryl group, in the same manner as the alkyl group, cycloalkyl group, or aryl group as $R_{204}$ to $R_{207}$ in the general formulae (ZI) to (ZIII).

A represents an alkylene group, alkenylene group, or arylene group.

More preferred compounds among the acid generators include compounds represented by the general formulae (ZI) to (ZIII).

Examples of the acid generators are described below, but the invention is not limited thereto.

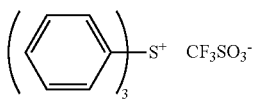
(z1)

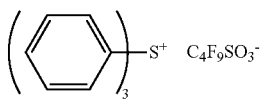
(z2)

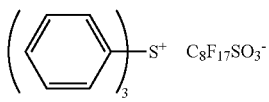
(z3)

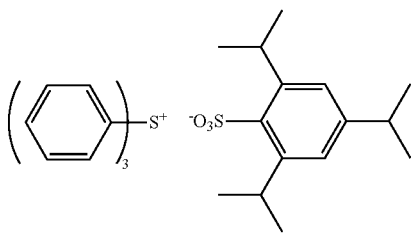
(z4)

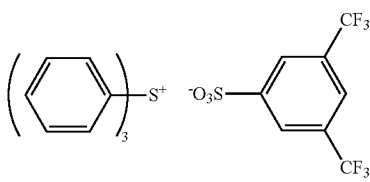
(z5)

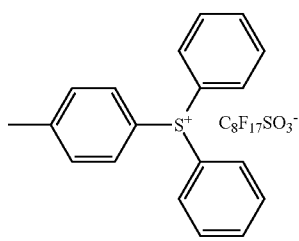
(z6)

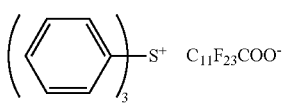
(z7)

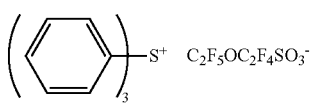
(z8)

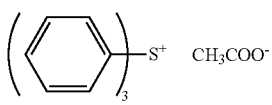

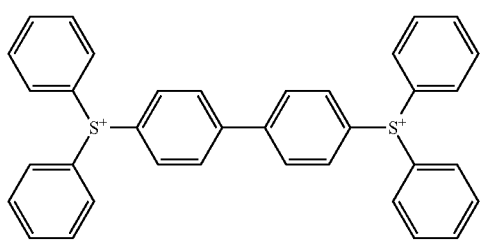
(z9)

(z10)

-continued
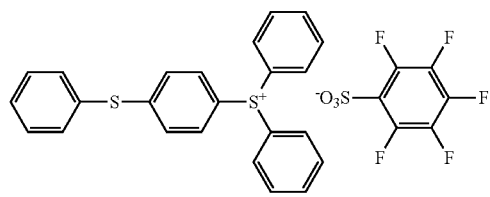 (z11)
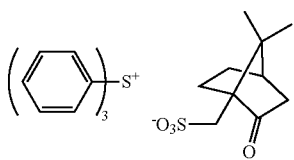 (z12)
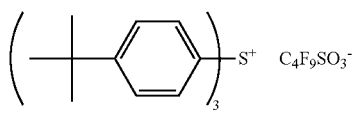 (z13)
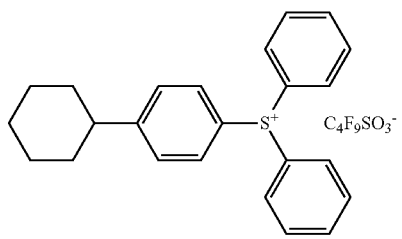 (z14)
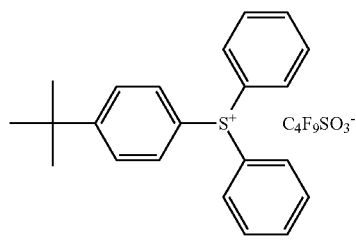 (z15)
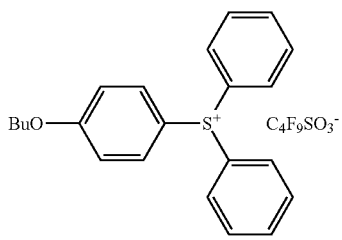 (z16)
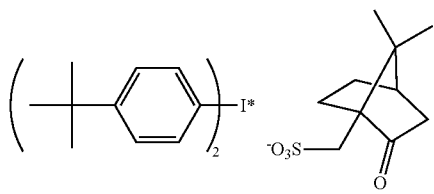 (z17)
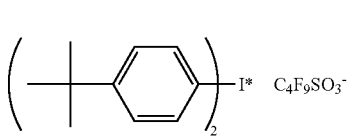 (z18)
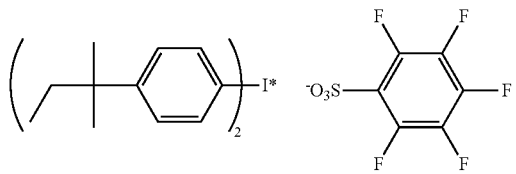 (z19)
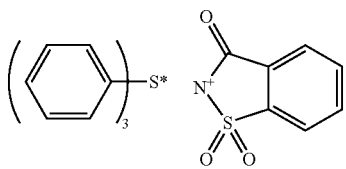 (z20)
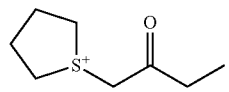 (z21)
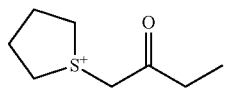 (z22)
CF$_3$SO$_3^-$
C$_4$F$_9$SO$_3^-$
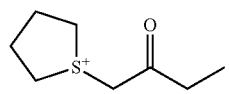 (z23)
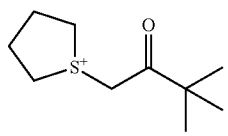 (z24)
C$_8$F$_{17}$SO$_3^-$
CF$_3$SO$_3^-$
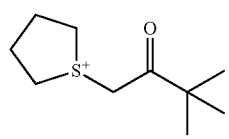 (z25)
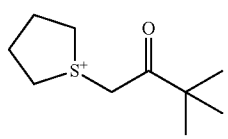 (z26)
C$_4$F$_9$SO$_3^-$
C$_8$F$_{17}$SO$_3^-$ -continued
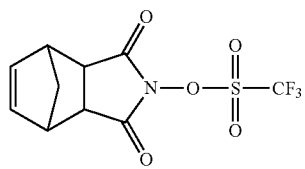
(z27)
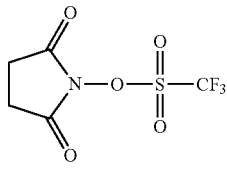
(z28)
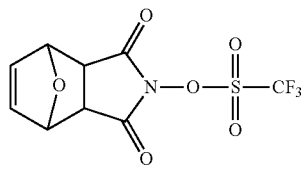
(z29)
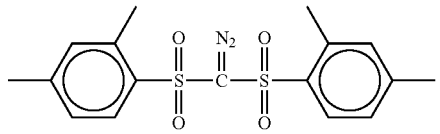
(z30)
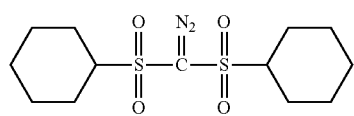
(z31)
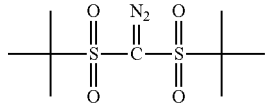
(z32)
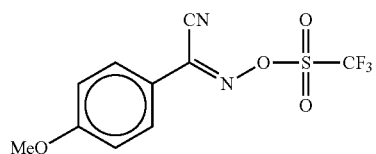
(z33)
(z34)
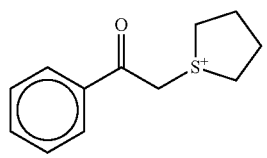
(z35)
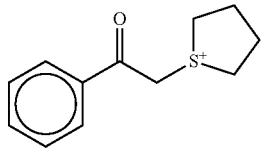
(z36)
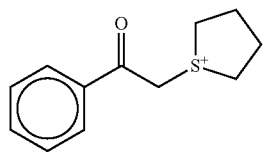
(z37)
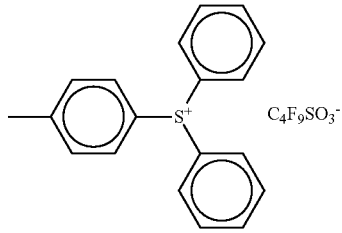
(z38)
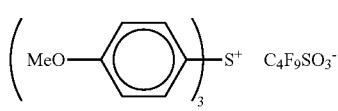
(z39)
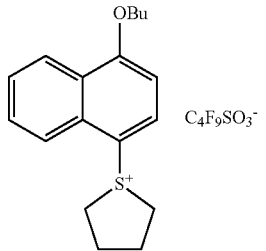
(z40)

-continued
(z41) 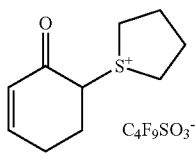
(z42) 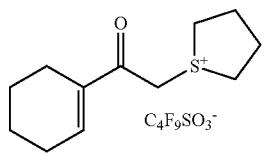
(z43) 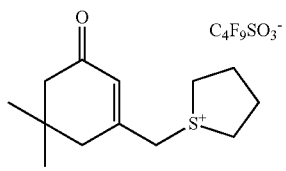
(z44) 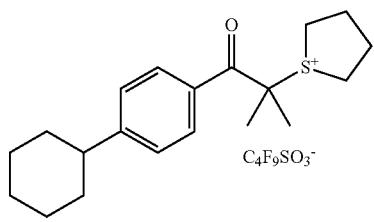
(z45) 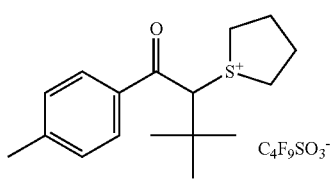
(z46) 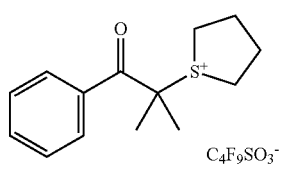
(z47) 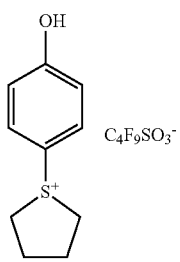
(z48) 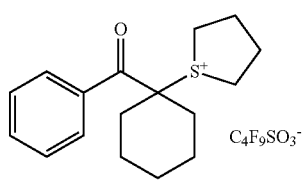
(z49) 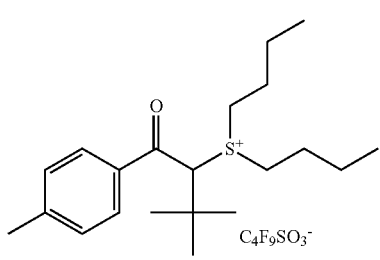
(z50) 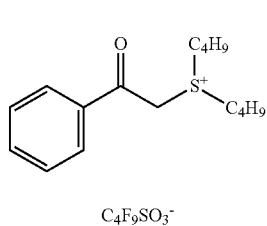
(z51) 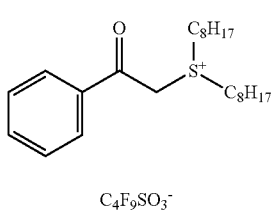
(z52) 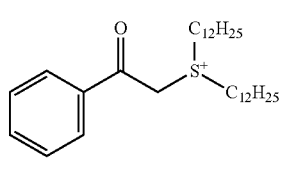
(z53) 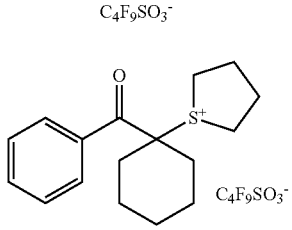
(z54) 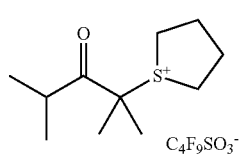

-continued
(z55) 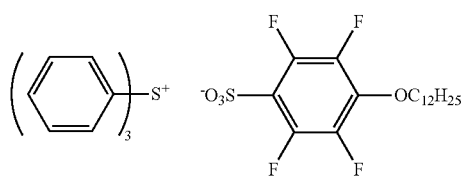
(z56) 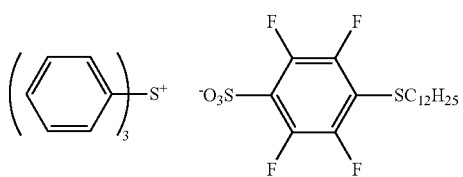
(z57) 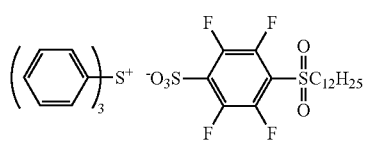
(z58) 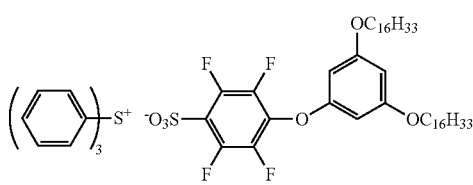
(z59) 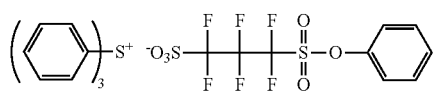
(z60) 
(z61) 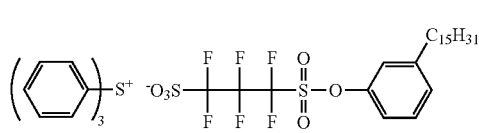
(z62) 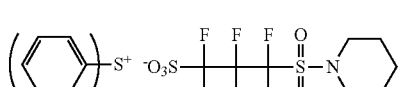
(z63) 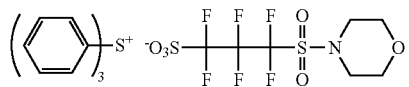
(z64) 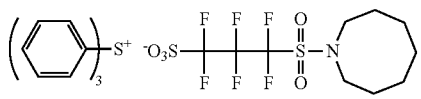
(z65) 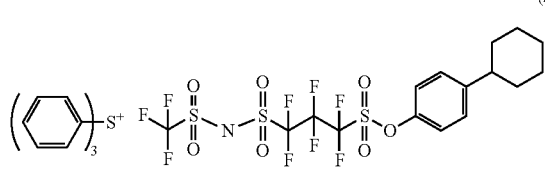
(z66) 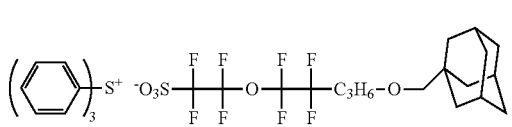
(z67) 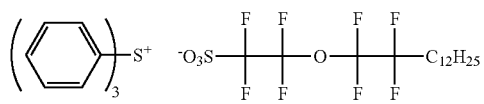
(z68) 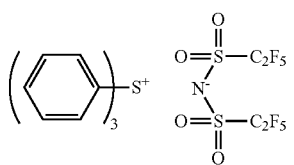
(z69) 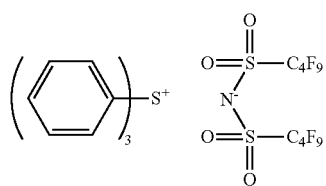
(z70) 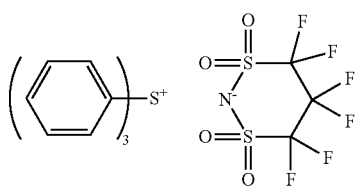
(z71) 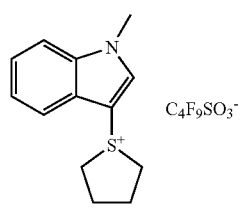
(z72) 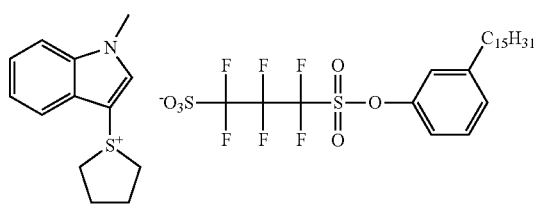

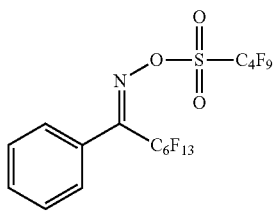 (z73)

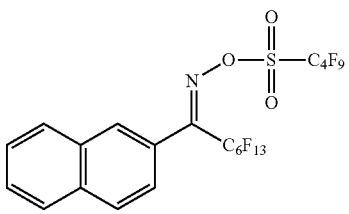 (z74)

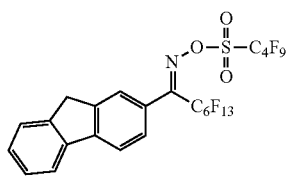 (z75)

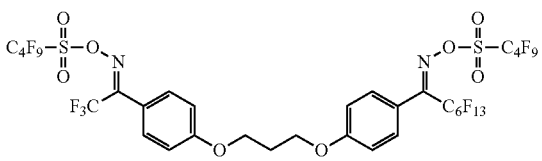 (z76)

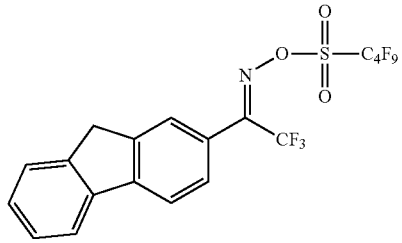 (z77)

The acid generators can be used each alone or as a combination of two or more of them.

The content of the acid generator in the positive type resist composition for liquid immersion exposure is preferably from 0.1 to 20 mass %, more preferably, from 0.5 to 10 mass %, further preferably, from 1 to 7 mass % based on the total solid content of the resist composition.

(C) Alkali Soluble Compound Having Alkyl Group of 5 or More Carbon Atoms.

The positive type resist composition for use in liquid immersion exposure according to the invention contains an alkali soluble compound (C) having an alkyl group of 5 or more carbon atoms.

Heretofore, when a resist with no problem in usual exposure is subjected to liquid immersion exposure, development defects occurred frequently. However, since penetration of water during liquid immersion exposure can be suppressed by the addition of the alkali soluble compound (C) having an alkyl group of 5 or more carbon atoms, development defects and scums can be decreased. Further, when the alkali soluble compound (C) is added to a resist with large leaching amount to the liquid immersion solution, the effect of suppressing leaching can be obtained.

The alkali soluble compound (C) is a compound which is alkali-soluble, that is, a compound soluble to an alkali developer (ordinarily, an aqueous alkaline solution having a pH of from 10.0 to 15.0 at 23° C.).

Therefore, the alkali-soluble compound (C) has an alkali soluble group and/or a group which is solubilized by hydrolyzation with an alkali developer.

The alkali soluble group includes, for example, a phenolic hydroxyl group, carboxylic acid group, fluorinated alcohol group, sulfonic acid group, sulfone amide group, (sulfonyl) (carbonyl) methylene group and active methylene group. Specific examples of the active methylene group include —C(=O)—CH$_2$—C(=O)—, —C(=O)—CHR—C(=O)— (where R represents an alkyl group), (—C(=O)—CH(C(=O))$_2$—, —SO$_2$—CH$_2$—C(=O)—), etc.

Preferred alkali-soluble group includes, for example, carboxylic acid group, fluorinated alcohol group (preferably, hexafluoroisopropanol), sulfonic acid group and sulfone amide group.

The group which is solubilized by hydrolyzation with an alkali developer includes, for example, a lactone group, ester group, sulfoneamide group, and acid anhydride, the lactone group, sulfoneamide group, and acid anhydride being preferred.

The amount of the alkali soluble group (acid group) is, preferably, from 2 to 10 mmeq/g and, more preferably, from 2 to 8 mmeq/g as an acid value of the alkali soluble compound (C). The acid value is based on the measurement of the amount of potassium hydroxide (mg) necessary for neutralizing the compound.

The alkali soluble compound (C) has an alkyl group of 5 or more carbon atoms.

The alkyl group of 5 or more carbon atoms is preferably linear or branched, and has preferably 6 or more carbon atoms, more preferably, 8 or more carbon atoms. The upper limit for the number of carbon atoms is preferably 100 or less, further preferably, 50 or less.

The alkyl group of 5 or more carbon atoms is preferably a fluorine-substituted alkyl group, particularly, a perfluoroalkyl group (for example, perfluorooctyl group or perfluorobutyl group).

The number of fluorine atoms present in the fluorine-substituted alkyl group is preferably from 5 to 100, more preferably, from 9 to 50.

The alkali-soluble compound (C) has alkyl groups of 5 or more carbon atoms in an amount, preferably, from 5 to 95 mass %, more preferably, from 10 to 80 mass % based on the molecular weight of the alkali soluble compound (C).

The alkali soluble compound may be either a low molecular compound or a high molecular compound (for example, a resin). The molecular weight is preferably, from 300 to 200,000, more preferably, from 500 to 200,000, further preferably, from 500 to 100,000.

In a case where the alkali soluble compound is a resin, those described below are preferred.
(a) The amount of residual monomers is, preferably, 0 to 10 mass %, further preferably, 0 to 5 mass %.
(b) The molecular weight distribution (Mw/Mn: also referred to as degree of dispersion) is usually within a range from 1 to 5, and those ranging, preferably, from 1 to 4, and further preferably from 1 to 3 are used. From the view point of resolution, resist configuration, side walls of resist patterns, and roughness, the molecular weight distribution is preferably 5 or less.

The addition amount of the alkali soluble compound (C) in the positive type resist composition for liquid immersion exposure is preferably from 1 to 60 mass %, more preferably from 1 to 40 mass %, most preferably from 1 to 10 mass % on the basis of the total solid content of the resist composition.

In a case where the positive type resist composition for liquid immersion exposure is a resist composition for ArF exposure, it is preferred that the alkali soluble compound contains no aromatic ring.

The alkali soluble compounds may be used each alone or a plurality of them may be mixed.

In a case where the alkali soluble compound is a resin, is can be synthesized by ordinary methods (for example, radical polymerization as in the synthesis of the acid decomposable resin (A) described above).

The alkali soluble compound (C) is preferably a resin comprising at least one repeating unit represented by the following general formulae (Ca) to (Cf).

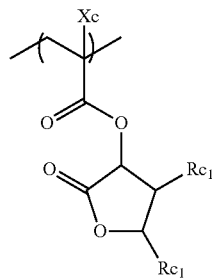

(Ca)

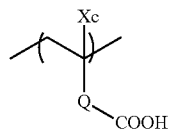

(Cb)

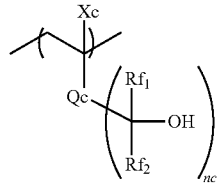

(Cc)

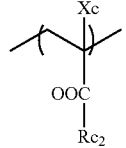

(Cd)

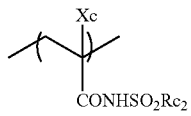

(Ce)

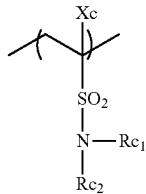

(Cf)

In the general formulae (Ca) to (Cf), Xc's each independently represents a hydrogen atom, a methyl group or an alkyl group having 5 or more carbon atoms.

$Rc_1$'s each independently represents a hydrogen atom, or an alkyl group having 5 or more carbon atoms.

$Rc_2$'s each independently represents an alkyl group having 5 or more carbon atoms.

$Rf_1$ and $Rf_2$ each independently represents a hydrogen atom or an alkyl group. At least one of $Rf_1$ and $Rf_2$ represents a fluorine-substituted alkyl group.

Q represents a single bond or a divalent linking group.

Qc represents a single bond or a (nc+1)-valent linking group.

nc represents a positive integer, preferably represents a integer of from 1 to 5, and more preferably represents a integer of 1 or 2.

The linking group preferably includes, although not particularly restricted, a single bond, alkylene group, cycroalkylene group, ether group, thioether group, carbonyl group, ester group, amide group, sulfoneamide group, urethane group and urea group, alone or in combination of two or more of them. Among them, alkylene group, cycroalkylene group and ester group alone or in combination of two or more of them are specifically preferred.

Specific examples of the high molecular weight alkali soluble compound (resin) are described below, but they are not restricted to them.

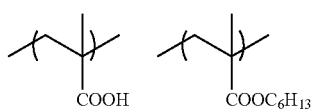

(C-1)

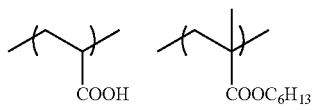

(C-2)

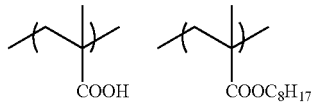

(C-3)

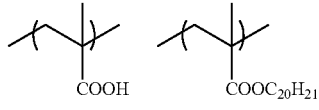

(C-4)

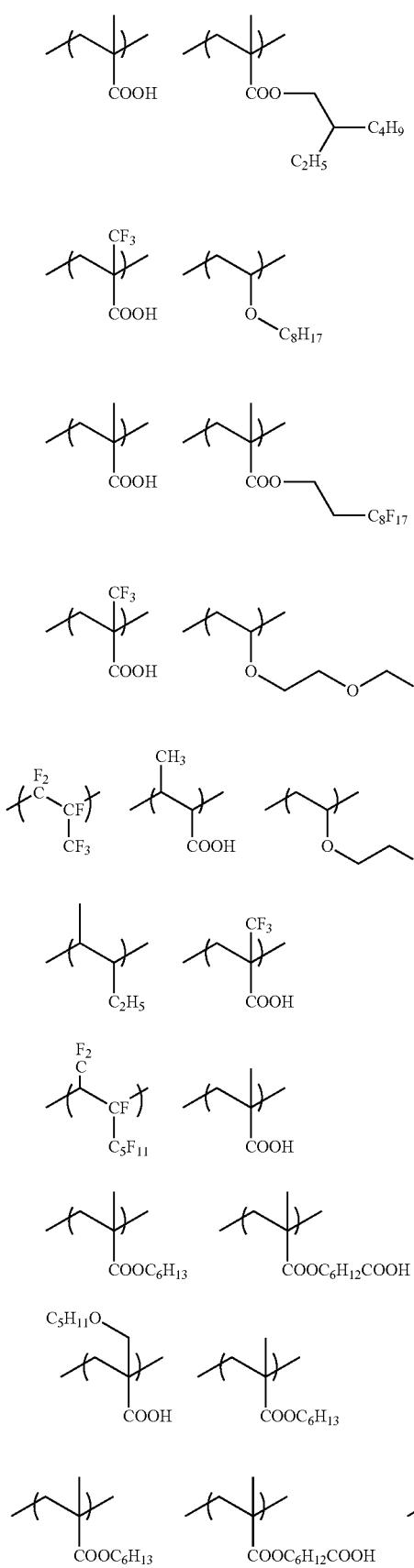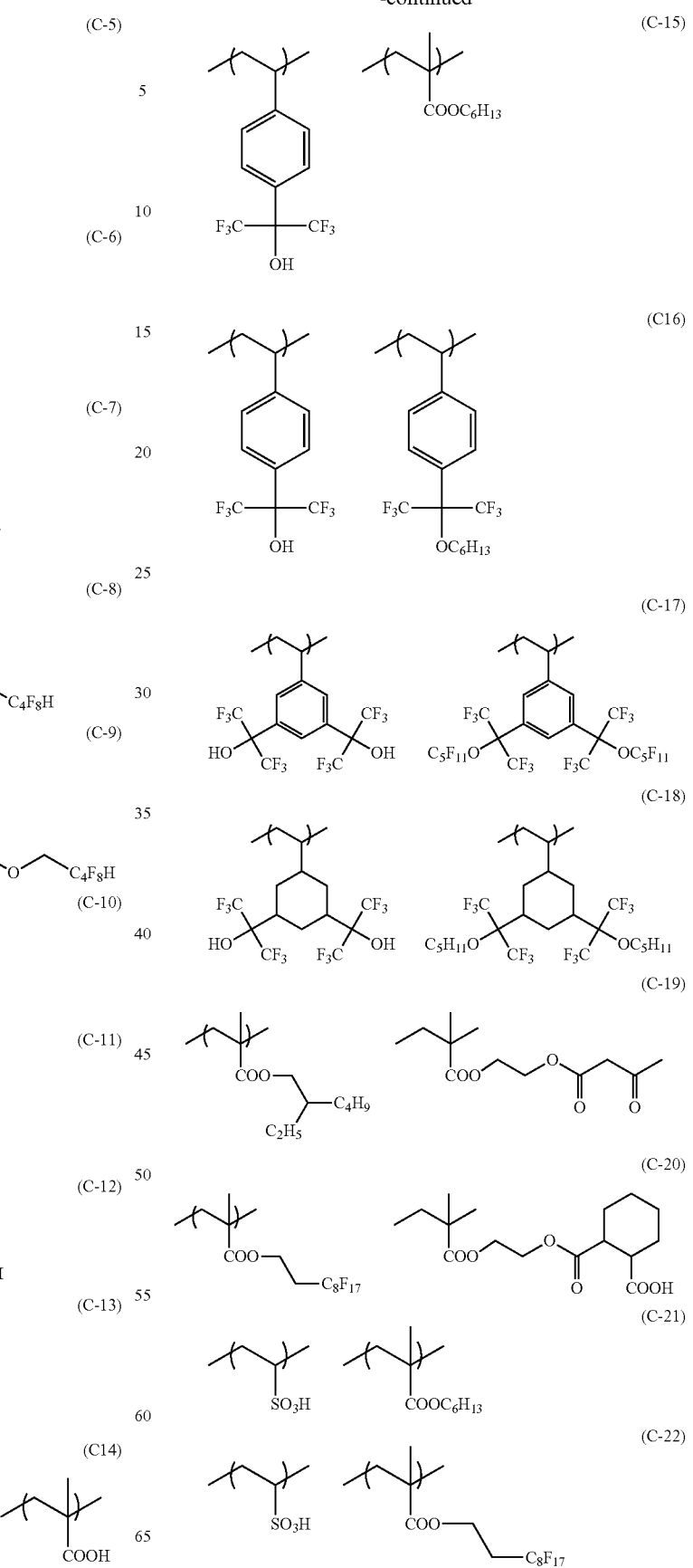

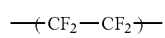 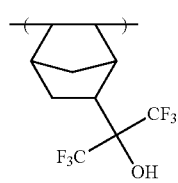 (C-23)
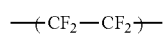 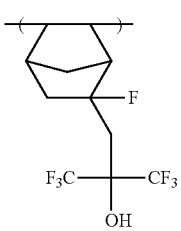 (C-24)
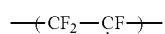 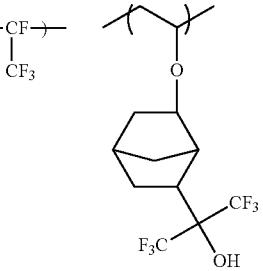 (C-25)
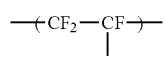 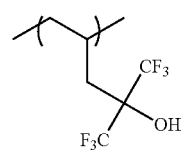 (C-26)
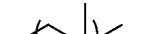 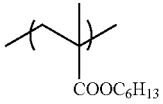 (C-27)
 
  (C-28)
 
  (C-29)
 
 
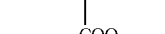 
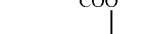 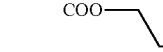
 
  (C-30)
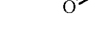 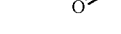 (C-31)
  (C-32)
  (C-33)
  (C-34)
 
  (C-35)
 
  (C-36)
 

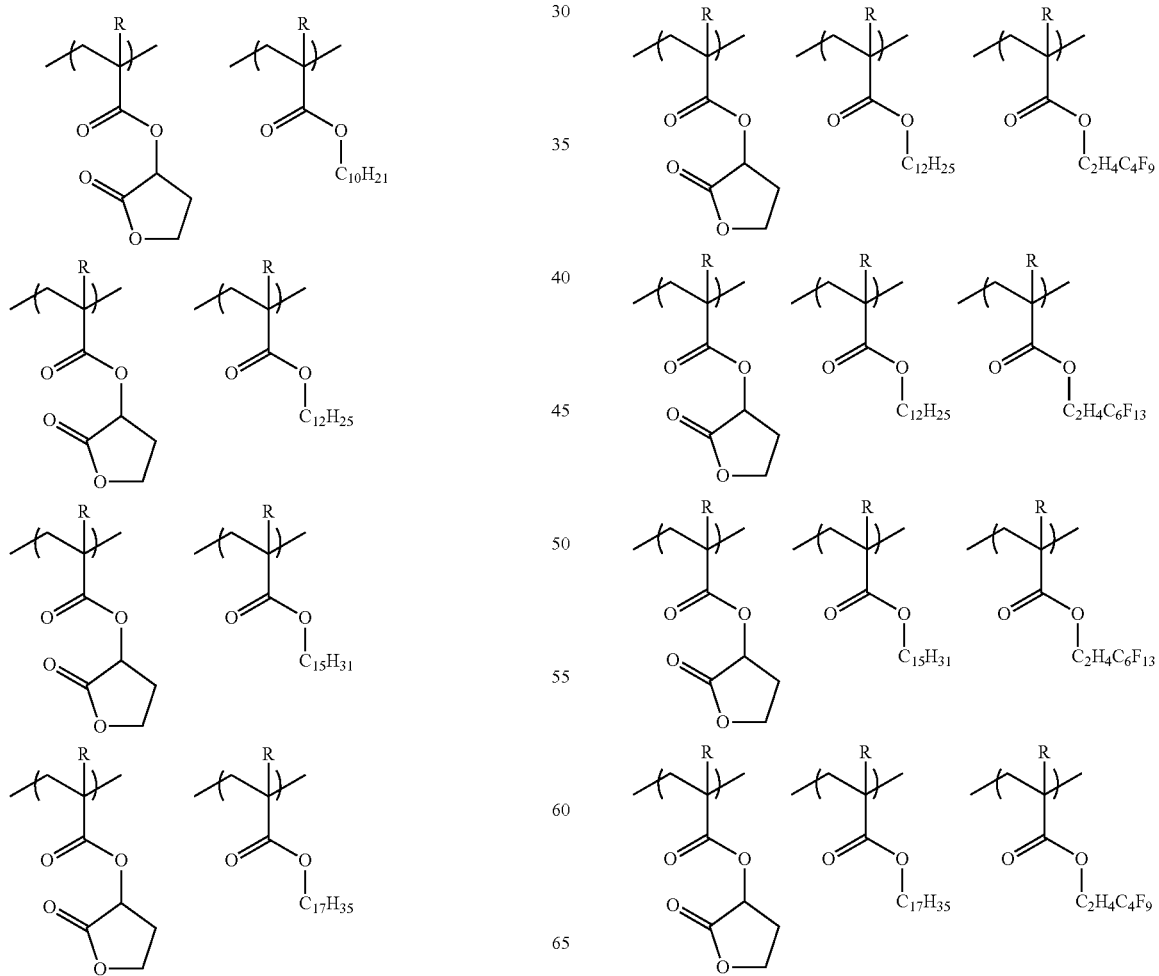

57
-continued
58
-continued
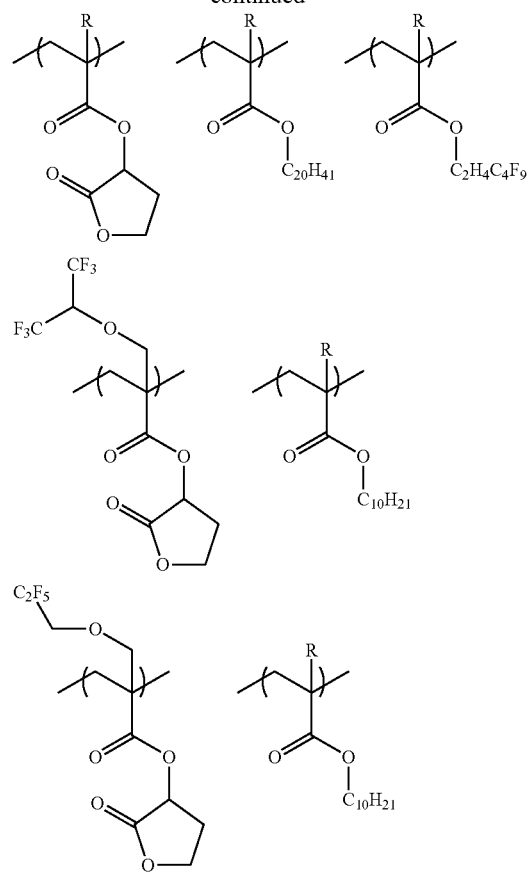
R = H, CH₃, F, CF₃, CH₂OH
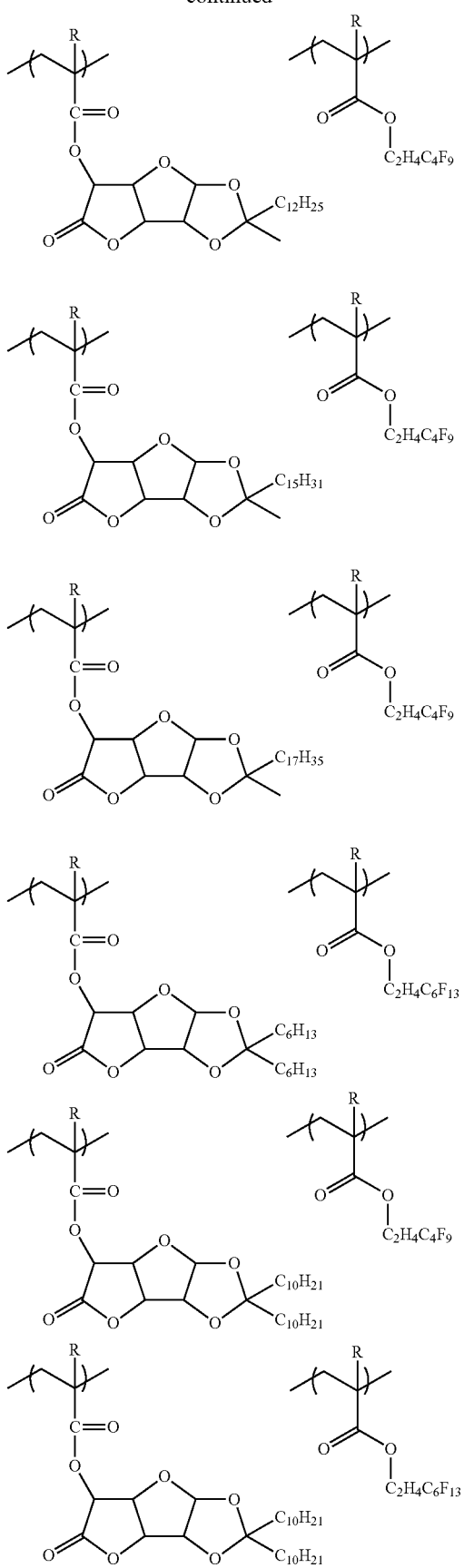

-continued
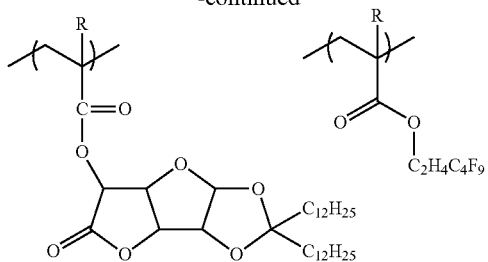
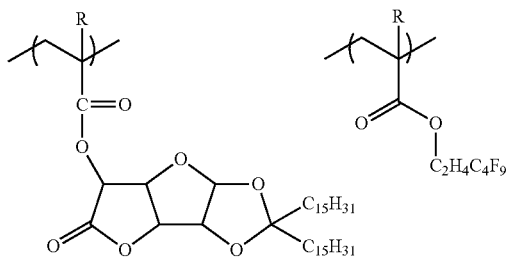
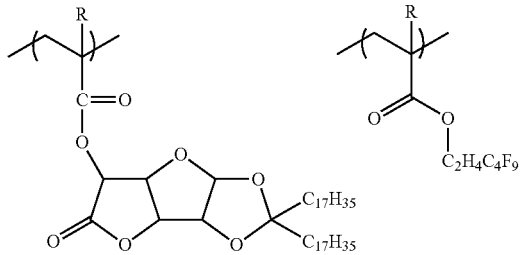
R = H, CH₃, F, CF₃, CH₂OH
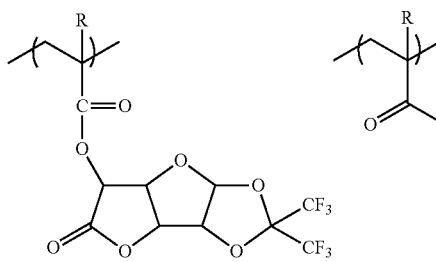
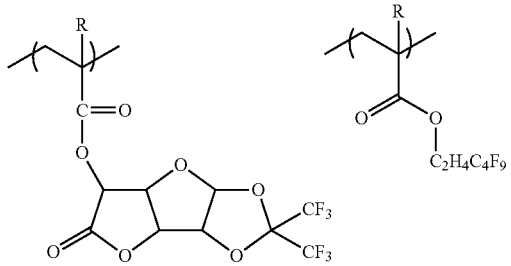
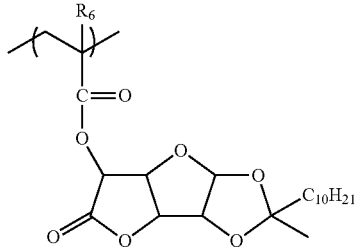
-continued
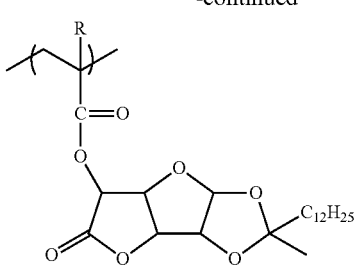
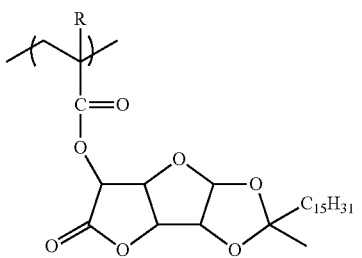
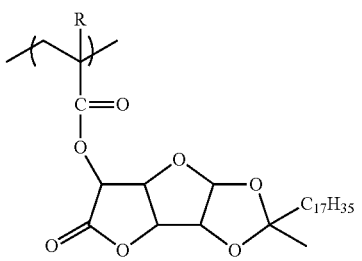
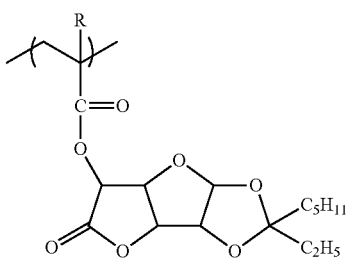
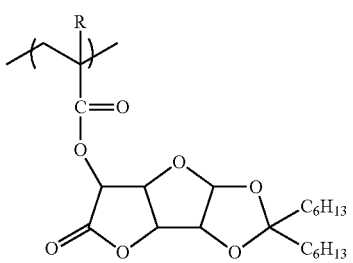
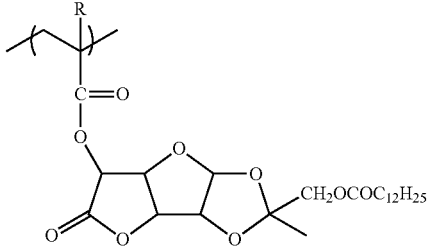

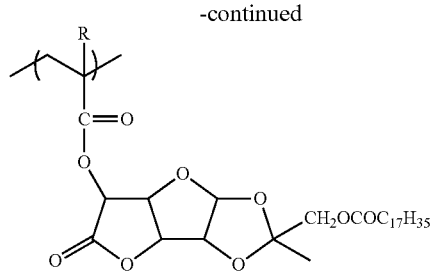
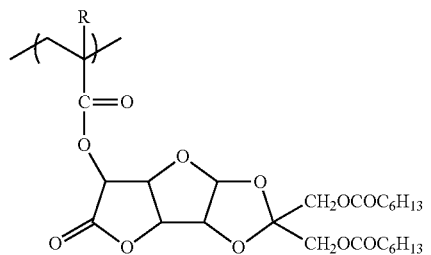
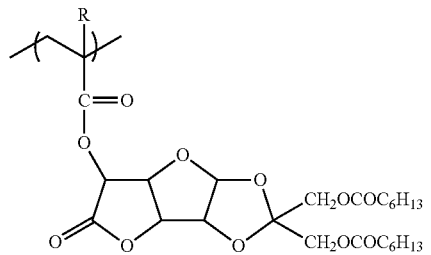
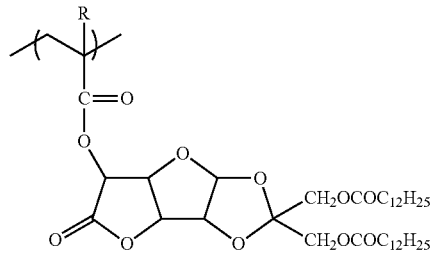
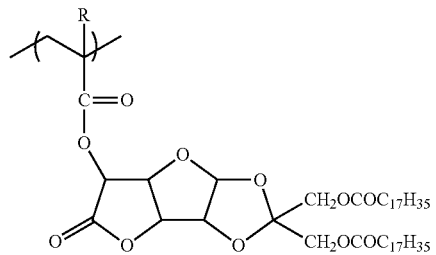
R = H, CH₃, F, CF₃, CH₂OH
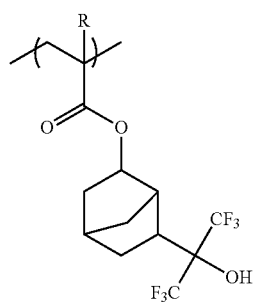
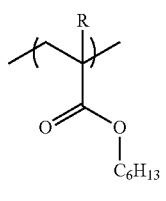
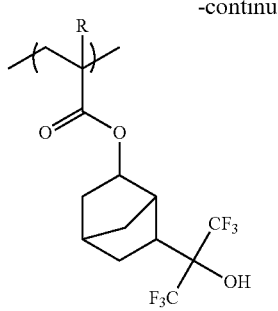
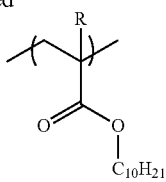
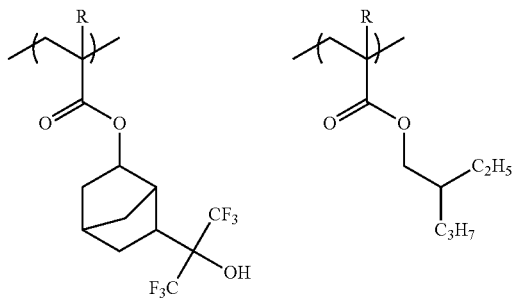
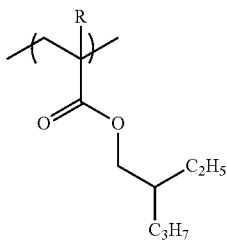
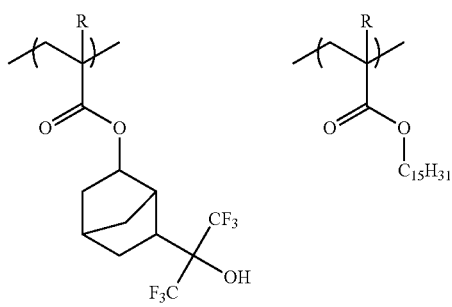
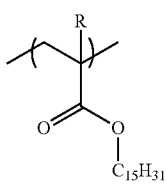
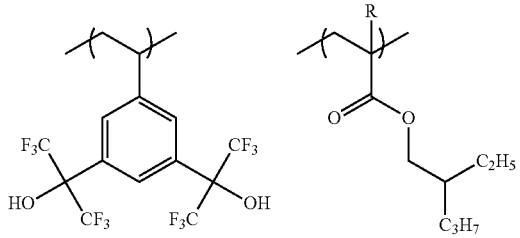
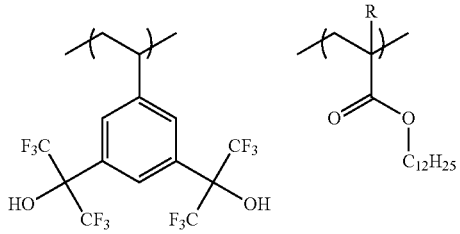
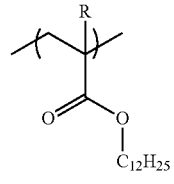
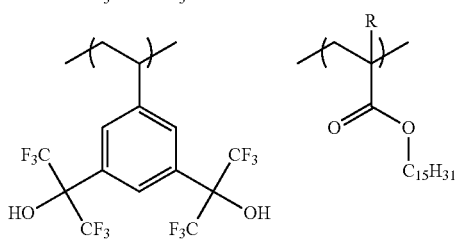
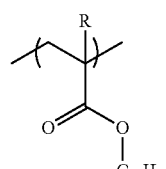

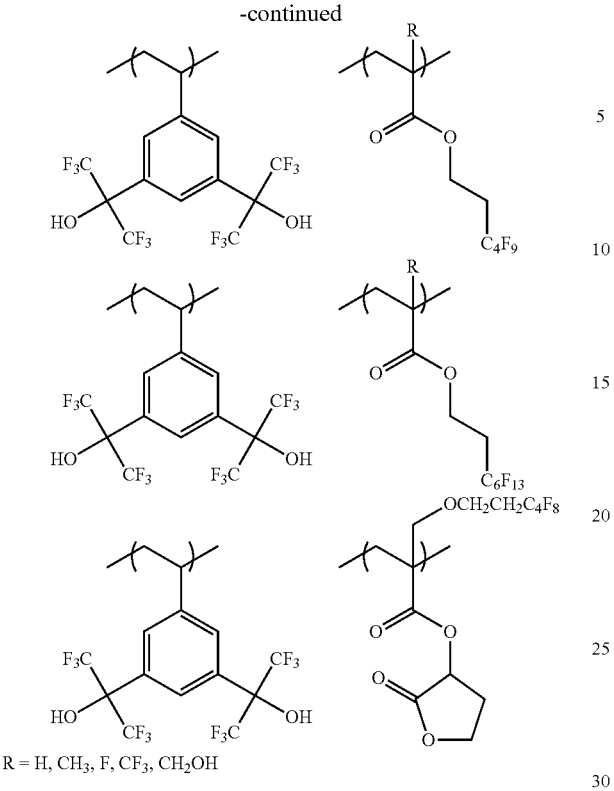

R = H, CH₃, F, CF₃, CH₂OH

A polymer containing a perfluoroalkyl group at the terminal end of the polymer can be synthesized by using a chain transfer agent substituted at the terminal end with the perfluoroalkyl group.

Examples of the low molecular weight alkali-soluble compound (C) are described below, but they are not restricted to the examples.

$C_{24}H_{49}COOH$ (E-1)

$C_{26}H_{53}COOH$ (E-2)

$C_{29}H_{59}COOH$ (E-3)

$HOOC-C_{22}H_{44}-COOH$ (E-4)

$C_9F_{19}COOH$ (E-5)

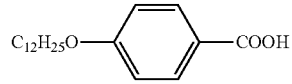 (E-6)

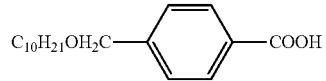 (E-7)

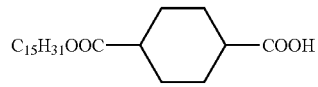 (E-8)

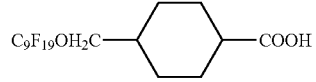 (E-9)

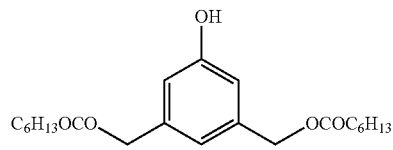 (E-10)

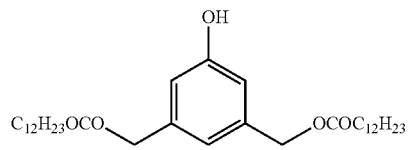 (E-11)

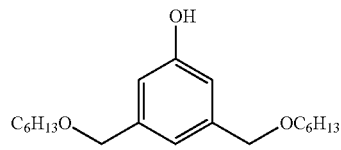 (E-12)

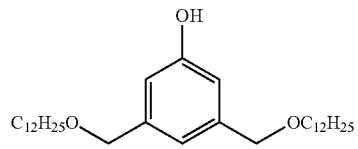 (E-13)

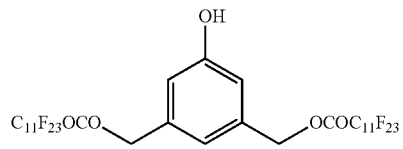 (E-14)

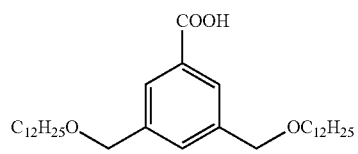 (E-15)

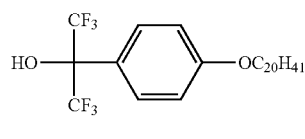 (E-16)

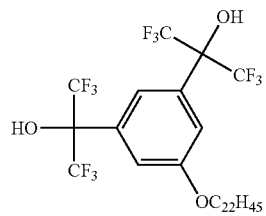 (E-17)

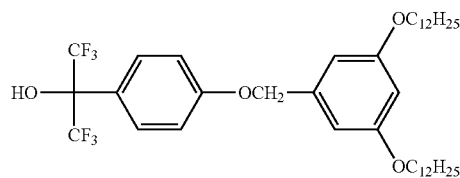 (E-18)

(E-19)
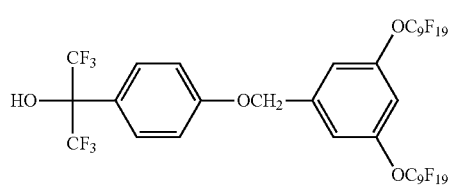

(E-20)
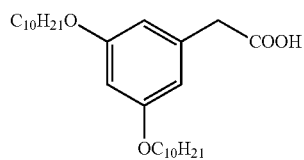

(E-21)
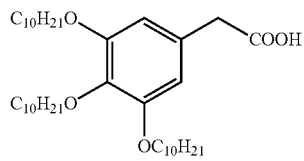

(E-22)
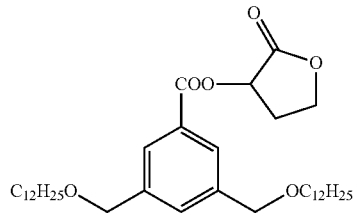

(E-23)
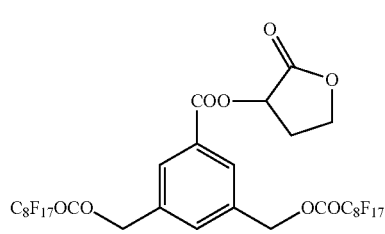

(E-24)
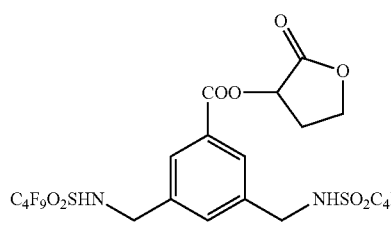

(E-25)

(E-26)
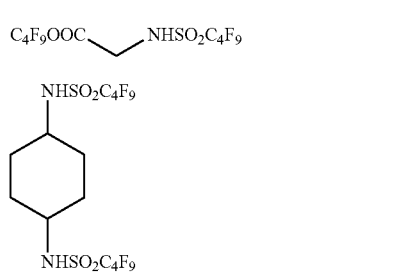

(D) Organic Solvent

The positive type resist composition for liquid immersion exposure according to the invention is used while being dissolved in a predetermined organic solvent.

The organic solvent which can be used includes, for example, ethylene dichloride, cyclohexanone, cyclopentanone, 2-heptanone, γ-butyrolactone, methylethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethyl formamide, dimethyl sulfoxide, N-methyl pyrrolidone, methoxy butanol, and tetrahydrofuran.

In the invention, a mixed solvent prepared by mixing a solvent having a hydroxyl group and a solvent having no hydroxyl group in the structure may be used as the organic solvent.

The solvent having a hydroxyl group includes, for example, ethylene glycol, ethylene glycol monomethyl ether, ethylene glycol monoethyl ether, propylene glycol, propylene glycol monomethyl ether, propylene glycol monoethyl ether and ethyl lactate. Among which propylene glycol monomethyl ether and ethyl lactate are preferred.

The solvent having no hydroxyl group includes, for example, propylene glycol monomethyl ether acetate, ethylethoxy propionate, 2-heptanone, γ-butyrolactone, cyclohexanone, butyl acetate, N-methyl pyrrolidone, N,N-dimethyl acetoamide and dimethyl sulfoxide, among which propylene glycol monomethyl ether acetate, ethyl ethoxy propionate, 2-heptanone, γ-butyrolactone, cyclohexanone, and butyl acetate are preferred, and propylene glycol monomethyl ether acetate, ethylethoxy propionate and 2-heptanone are more preferred.

The mixing ratio (mass) of the solvent having a hydroxyl group and the solvent having no hydroxyl group is preferably, from 1/99 to 99/1, more preferably, from 10/90 to 90/10, further preferably, from 20/80 to 60/40. A mixed solvent containing 50 mass % or more of the solvent having no hydroxyl group is particularly preferred in view of the uniformity upon coating.

By using such a solvent, a resist composition at a solid concentration usually from 3 to 25 mass %, preferably, from 5 to 22 mass %, more preferably, from 7 to 20 mass %, further preferably, from 5 to 15 mass % is prepared.

(E) Organic Basic Compound

The composition of the invention, with an aim of preventing aging fluctuation of the performance after the irradiation of the actinic ray or the radiation to the heat treatment (T-tope shape formation of the pattern, sensitivity fluctuation, fluctuation of pattern line width, etc.), aging fluctuation of performance after coating and, further, excessive diffusion of acid (degradation of resolution) after irradiation of the actinic ray or the radiation and during heat treatment, an organic basic compound can be used. The organic basic compound is, for example, an organic basic compound containing a basic nitrogen, and those compounds with a pKa value of a conjugated acid of 4 or more are used preferably.

Specifically, the following formulae (A) to (E) can be mentioned.

(A)
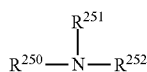

(B)
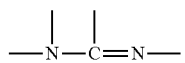

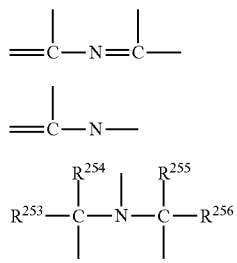

(C), (D), (E)

where $R^{250}$, $R^{251}$ and $R^{252}$ may be identical with or different from each other, and each represents an alkyl group of 1 to 20 carbon atoms, cycloalkyl group of 1 to 20 carbon atoms, or aryl group of from 6 to 20 carbon atoms, in which $R^{251}$ and $R^{252}$ may join to each other to form a ring. A substituent which may be present in each of the groups includes an amino group and hydroxyl group.

$R^{253}$, $R^{254}$, $R^{255}$ and $R^{256}$ may be identical with or different from each other, and each represents an alkyl group of 1 to 6 carbon atoms.

Preferred examples include, for example, guanidine, aminopyridine, aminoalkylpyridine, aminopyrrolidine, indazole, imidazole, pyrazole, pyrazine, pyrimidine, purine, imidazoline, pyrazoline, piperazine, aminomorpholine, and aminoalkyl morpholine. Those compounds may have a substituent, and preferred substituent includes, for example, an amino group, aminoalkyl group, alkylamino group, aminoaryl group, arylamino group, alkyl group, alkoxy group, acyl group, acyloxy group, aryl group, aryloxy group, nitro group, hydroxyl group, and cyano group.

Particularly preferred compounds include, for example, guanidine, 1,1-dimethyl guanidine, 1,1,3,3-tetramethyl guanidine, imidazole, 2-methylimidazole, 4-methyl imidazole, N-methyl imidazole, 2-phenylimidazole, 4,5-diphenyl imidazole, 2,4,5-triphenyl imidazole, 2-aminopyridine, 3-aminopyridine, 4-aminopyridine, 2-dimemthylamino pyridine, 4-dimethylamino pyridine, 2-diethyl aminopyridine, 2-(aminomethyl)pyridine, 2-amino-3-methyl pyridine, 2-amino-4-methyl pyridine, 2-amino-5-methyl pyridine, 2-amino-6-methyl pyridine, 3-aminoethyl pyridine, and 4-aminoethyl pyridine.

3-aminopyrolidine, piperazine, N-(2-aminoethyl) peperazine, N-(2-aminoethyl)pyperidine, 4-amino-2,2,6,6-tetramethyl piperidine, 4-piperidino piperidine, 2-iminopiperidine, 1-(2-aminoethyl)pyrrolidine, pyrazole, 3-amino-5-methyl pyrazole, 5-amino-3-methyl-1-p-tolylpyrazole, pyrazine, 2-(aminomethyl)-5-methyl pyrazine, pyrimidine, 2,4-diaminopyrimidine, 4,6-dihydroxypyrimidine, 2-pirazoline, 3-pirazoline, N-aminomorpholine, and N-(2-aminoethyl)morpholine, but, they are not restricted to them.

In addition, basic ammonium salts can be used. Specific examples of the basic ammonium salts can include those compounds described below, but they are not restricted to them.

Specifically, they include ammonium hydroxide, ammonium triflate, ammonium pentaflate, ammonium heptaflate, ammonium nonaflate, ammonium undecaflate, ammonium tridecaflate, ammonium pentadecaflate, ammonium methyl carboxylate, ammonium ethyl carboxylate, ammonium propyl carboxylate, ammonium butyl carboxylate, ammonium heptyl carboxylate, ammonium hexyl carboxylate, ammonium octyl carboxylate, ammonium nonyl carboxylate, ammonium decylcarboxylate, ammonium undecylcarboxylate, ammonium dodecadecyl carboxylate, ammonium tridecyl carboxylate, ammonium tetradecyl carboxylate, ammonium pentadecyl carboxylate, ammonium hexadecyl carboxylate, ammonium heptadecyl carboxylate, and ammonium octadecyl carboxylate.

The ammonium hydroxide described above includes specifically, tetramethyl ammonium hydroxide, tetraethyl ammonium hydroxide, tetrapropyl ammonium hydroxide, tetrabutyl ammonium hydroxide, tetrapentyl ammonium hydroxide, tetrahexyl ammonium hydroxide, tetraheptyl ammonium hydroxide, methyl trioctyl ammonium hydroxide, tetraoctyl ammonium hydroxide, didecyldimethyl ammonium hydroxide, tetrakisdecyl ammonium hydroxide, dodecyl trimethyl ammonium hydroxide, dodecylethyl dimethyl ammonium hydroxide, didodecyl dimethyl ammonium hydroxide, tridodecylmethyl ammonium hydroxide, myristylmethyl ammonium hydroxide, dimethylditeradecyl ammonium hydroxide, hexadecyl trimethyl ammonium hydroxide, octadecyl trimethyl ammonium hydroxide, dimethyl dioctadecyl ammonium hydroxide, tetraoctadecyl ammonium hydroxide, diallyldimethyl ammonium hydroxide, (2-chloroethyl)-trimethyl ammonium hydroxide, (2-bromoethyl)trimethyl ammonium hydroxide, (3-bromopropyl)-trimethyl ammonium hydroxide, (3-bromopropyl)triethyl ammonium hydroxide, glycidyl trimethyl ammonium hydroxide, choline hydroxide, (R)-(+)-(3-chloro-2-hydroxypropyl)trimethyl ammonium hydroxide, (S)-(−)-(3-chloro-2-hydroxypropyl)-trimethyl ammonium hydroxide, (3-chloro-2-hydroxypropy)-trimethyl ammonium hydroxide, (2-aminoethyl)-trimethyl ammonium hydroxide, hexamethonium hydroxide, decamethonium hydroxide, 1-azoniaproperane hydroxide, petronium hydroxide, 2-chloro-1,3-dimethyl-2-imidazolinium hydroxide, and 3-ethyl-2-methyl-2-thiazolinium hydroxide.

The organic basic compounds can be used by one or more and more preferably, by two or more of them.

The amount of the organic basic compound to be used is usually, from 0.001 to 10 mass %, preferably, from 0.01 to 5 mass % on the basis of the solid content of the positive type resist composition for liquid immersion exposure.

The ratio between the acid generator and the organic basic compound to be used in the composition, that is, acid generator/organic basic compound (molar ratio) is, preferably, from 2.5 to 300. Namely, the molar ratio is preferably 2.5 or more in view of the sensitivity and the resolution, and is preferably 300 or less in view of suppression of degradation of the resolution due to the thickening with the of the resist pattern up to the heating treatment after exposure. The acid generator/organic basic compound (molar ratio) is, more preferably, from 5.0 to 200, further preferably, from 7.0 to 150.

(F) A Dissolution Inhibitive Compound which is Decomposed Under the Effect of Acid and Increases the Solubility in an Alkali Developer The positive type resist composition for use in liquid immersion exposure according to the invention can contain a solution inhibitive compound that is decomposed under the effect of an acid and increases the solubility in the alkali developer (hereinafter also referred to as a "solution inhibitive compound").

As the solution inhibitive compound, cycloaliphatic compounds or aliphatic compounds containing acid decomposable groups such as cholic acid derivatives containing acid decomposable groups as described in the proceeding of SPIE, 2724, 355 (1996) are preferred in order not to lower the transmittance at 220 nm or less. The acid decomposable group and the cycloaliphatic structure include those identical as described for the acid decomposable resin (A).

The molecular weight of the solution inhibitive compound is, preferably, 3,000 or less, more preferably, from 300 to 3,000 and, further preferably, from 500 to 2,500.

The addition amount of the dissolution inhibitive compound is, preferably, from 1 to 30 mass %, more preferably, from 2 to 20 mass % based on the entire solid content of the positive type resist composition for liquid immersion exposure.

Specific examples of the dissolution inhibitive compound is to be described below, but it is not restricted to them.

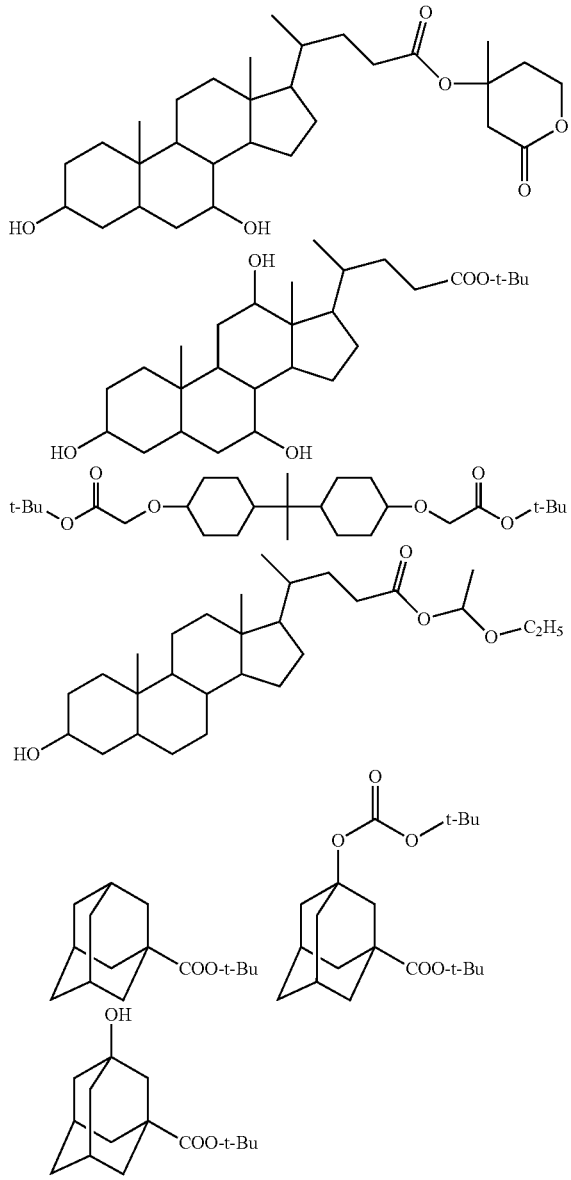

(G) Surfactant

The positive type resist composition for liquid immersion exposure according to the invention can further contain a surfactant (G). The surfactant includes preferably, a fluorine-based and/or a silicon-based surfactant (a fluorine-based surfactant, a silicon-based surfactant, or a surfactant having both a fluorine atom and a silicon atom), or two or more of them.

Since the resist composition for liquid immersion exposure according to the invention contains the surfactant (G), it has enhancing effect on the sensitivity, resolution, adhesiveness, suppression of development failure, etc. upon use of exposure light source at 250 nm or less, particularly, 220 nm or less.

The fluorine-based and/or silicon-based surfactants, can include surfactants disclosed in, for example, JP-A Nos. 62-36663, 61-226746, 61-226745, 62-170950, 63-34540, 7-230165, 8-62834, 9-54432, 9-5988, Japanese Patent Application No. 2002-277862, U.S. Pat. Nos. 5,405,720, 5,360, 692, 5,529,881, 5,296,330, 5,436,098, 5,576,143, 5,294,511, and 5,824,451, and commercially available surfactants described below can also be used as they are.

Commercially available surfactants include, for example, fluorine-based or silicone-based surfactants such as F-top EF301, and EF303 (manufactured by Shin-Akita Kasei K.K.), Florad FC430, 431 and 4430 (manufactured by Sumitomo 3M, Inc.), Megafac F171, F173, F176, F189, F113, F110, F117, F120 and R08 (manufactured by Dainippon Ink and Chemicals, Inc.), Surflon S-382, SC101, 102, 103, 104, 105, and 106, (manufactured by Asahi Glass Co., Ltd.), Troysol S-366 (manufactured by Troy Chemical Industries, Inc.), F-top EF121, EF122A, EF122B, RF122C, EF125M, EF135M, EF351, 352, EF801, EF802, EF 601 (manufactured by JEMCO Inc.), PF636, PF656, PF6320, PF6520 (manufactured by OMNOVA SOLUTIONS, INC.), FTX-204D, 2080, 2180, 230G, 204D, 208D, 212D, 218, 222D (manufactured by NEOS) etc. Further, a polysiloxane polymer KP-341 (manufactured by Shin-Etsu Chemical Co., Ltd.) can also be used as the silicon-based surfactant.

In addition to the known surfactants described above, surfactants using polymers having a fluoro aliphatic group derived from a fluoro aliphatic compound produced by a telomerization method (also referred to as a telomer method) or an oligomerization method (also referred to as oligomer method) can also be used. The fluoro aliphatic compound can be synthesized by a method described in JP-A No. 2002-90991.

As the polymer having a fluoro aliphatic group, copolymers of monomers having a fluoro aliphatic group and a (poly(oxyalkylene))acrylate and/or (poly(oxyalkylene))methacrylate are preferred, and they may be distributed at random or block-copolymerized. The poly(oxyalkylene) group includes poly(oxyethylene) group, poly(oxypropylene) group, poly(oxybutylene) group, etc, and, in addition, may be a unit having alkylenes of different chain length in the same chain, for example, poly(block-connected form of oxyethylene and oxypropylene and oxyethylene) and poly(block connection form of oxyethylene and oxypropylene), etc. Further, the copolymer of the monomers having a fluoro aliphatic group and (poly(oxyalkylene))acrylate (or methacrylate) includes not only binary copolymers but also ternary or higher copolymers formed by simultaneously copolymerizing monomers having two or more different fluoro aliphatic groups and two or more different (poly(oxyalkylene))acrylates (or methacrylates).

For example, the commercially available surfactants include Megafac F178, F-470, F-473, F-475, F-476, and F-472 (manufactured by Dainippon Ink and Chemicals, Inc.). In addition, they include copolymers of acrylate (or methacrylate) having a $C_6F_{13}$ group and (poly(oxyalkylene))acrylate (or methacrylate), and copolymers of acrylate (or methacrylate) having a $C_3F_7$ group, (poly(oxyethylene)) acrylate (or methacrylate) and (poly(oxypropylene)) acrylate (or methacrylate), etc.

In the invention, surfactants other than the fluorine-based and/or silicon-based surfactants can also be used. Specifically, they include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkyl allyl ethers such as polyoxyethylene octyl phenol ether and polyoxyethylene nonyl phenol ethers, sorbitan fatty acid esters such as polyoxyethylene.polyoxypropylene block copolymers, sorbitan monolaurate, sorbitan monopalmitate, sorbitan monostearate, sorbitan monooleate, sorbitan trioleate, and sorbitan tristearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate.

In the invention, surfactants represented by the following general formula (W) may also be used.

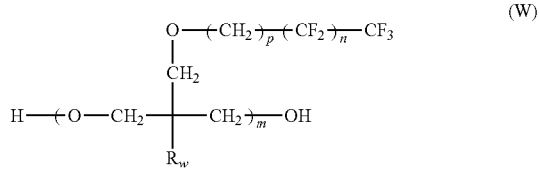

In the general formula (W),
$R_w$ represents a hydrogen atom or an alkyl group,
m represents an integer of 1 to 30,
n represents 0 or an integer of 1 to 3, and
p represents 0 or an integer of 1 to 5.

The alkyl group in $R_w$ is preferably a linear or branched alkyl group of 1 to 5 carbon atoms and includes, for example, a methyl group, ethyl group, propyl group, n-butyl group, sec-butyl group, and t-butyl group. Among them, methyl group, ethyl group and propyl group are preferred.

In the general formula (W), it is preferred that m represents an integer of 1 to 25, n is an integer of 0 to 2, and p is an integer of 0 to 3.

Preferred examples of the surfactant represented by the general formula (W) include, for example, commercially available PF 636 (n=0, m=6, p=1, and $R_1$=methyl group in the general formula (W)), PF 6320 (n=0, m=20, p=1, and $R_1$=methyl group), PF656 (n=1, m=6, p=1, and $R_1$=methyl group in the general formula (W), and PF 6520 (n=1, m=20, p=1, and $R_1$=methyl group in the general formula (W)), (all manufactured by OMNOVA SOLUTIONS, INC.).

The surfactants may be used each alone, or may be used as a combination of several of them.

The amount of surfactant (G) to be used is preferably, from 0.01 to 5 mass %, more preferably, from 0.1 to 3 mass % based on the entire amount of the resist composition for liquid immersion exposure (except for solvent).

(H) Alkali Soluble Resin

The positive type resist composition for liquid immersion exposure according to the invention can further be incorporated with a resin which is soluble to an alkali developer, whereby the sensitivity is improved.

In the invention, novolac resins having a molecular weight of 1,000 to 20,000 or polyhydroxystyrene derivatives having a molecular weight of about from 3,000 to 50,000 can be used as such a resin. However, since they have large absorption relative to the light of 250 nm or less, it is preferred that they are used while being partially hydrogenated, or used in an amount of 30 mass % or less based on the entire amount of the resin.

In addition, resins having a carboxyl group as an alkali soluble group may also be used. The resin having the carboxyl group preferably has a mono-nuclear or poly-nuclear cycloaliphatic hydrocarbon group for improving the dry etching resistance. Specifically, they include a copolymer of a methacrylic acid ester having a cycloaliphatic hydrocarbon structure showing no acid decomposability and a (meth) acrylic acid or a resin of (meth)acrylic acid ester of a cycloaliphatic hydrocarbon group having a carboxyl group at the terminal.

The addition amount of such alkali soluble resin is usually 30 mass % or less based on the total amount of the resin including the acid decomposable resin (A).

(I) Carboxylic Acid Onium Salt

The positive type resist composition for liquid immersion exposure according to the invention may be incorporated with a carboxylic acid onium salt.

The carboxylic acid onium salts in the invention includes carboxylic acid sulfonium salt, carboxylic acid iodonium salts, carboxylic acid ammonium salts, etc. Particularly, as the carboxylic acid onium salts, iodonium salts and sulfonium salts are preferred. Further, it is preferred that the carboxylate residue in the carboxylic acid onium salt contains no aromatic group or carbon-carbon double bond. Especially preferred anion moiety includes linear, branched, mononuclear or polynuclear alkyl carboxylic acid anions having 1 to 30 carbon atoms. Further anions of carboxylic acid in which the alkyl groups are partially or entirely substituted with fluorine are more preferred. The alkyl chain may be incorporated with oxygen atoms. This can ensure the transparency relative to the light of 220 nm or less, improve the sensitivity and resolution, and improve the density dependence and exposure margin.

The anions of fluoro-substituted carboxylic acid include anions of fluoroacetic acid, nonafluoropentanoic acid, perfluorododecanoic acid, perfluorotridecanoic acid, difluoroacetic acid, trifluoroacetic acid, pentafluoropropionic acid, heptafluorobutyric acid, perfluorocyclohexane carboxylic acid, 2,2-bistrifluoromethyl propionic acid, etc.

Those carboxylic acid onium salts can be synthesized by reacting sulfonium hydroxide, iodonium hydroxide, ammonium hydroxide, on carboxylic acid with a silver oxide in an appropriate solvent.

The content of the carboxylic acid onium salt in the composition is appropriately from 0.1 to 20 mass %, preferably, from 0.5 to 10 mass %, further preferably, from 1 to 7 mass % based on the total solid content of the positive type resist composition for liquid immersion exposure.

(J) Other Additives

The positive resist composition for liquid immersion exposure can further be incorporated optionally with dyes, plasticizers, photosensitizers and compounds for accelerating the solubility to liquid developer (for examples, phenol compounds having a molecular weight of 1,000 or less, cycloaliphatic or aliphatic compounds having a carboxylic group), etc.

Such phenol compounds having a molecular weight of 1,000 or less can easily be synthesized by those skilled in the art with reference to the method described in JP-A Nos. 4-122938, and 2-28531, and U.S. Pat. No. 4,916,210, and EP No. 219,294.

Specific examples of the cycloaliphatic or aliphatic compounds having a carboxylic group include carboxylic acid derivatives having a steroid structure such as cholic acid, deoxycholic acid, and lithocholic acid, adamantane carboxylic acid derivatives, adamantane dicarboxylic acid, cyclohexane carboxylic acid and cyclohexane dicarboxylic acid, but they are not restricted to them.

The metal content in the positive type resist composition for liquid immersion exposure of the invention is preferably 100 ppb or less.

(K) Pattern Forming Method

The positive type resist composition for liquid immersion exposure according to the invention is used by dissolving the ingredients described above in a predetermined organic solvent, preferably, the mixed solvent described above, and then coating it on a predetermined support as described below.

Namely, the positive type resist composition for liquid immersion exposure is coated at a predetermined thickness (usually, from 50 to 500 nm) on a substrate (for example, silicone/silicon dioxide coating) which is used for the manufacture of precise integrated circuit elements by an appropriate coating method such as by a spinner or a coater.

After coating, the resist is dried by spinning or baking to form a resist film, then subjected to exposure by way of a liquid immersion solution (liquid immersion exposure) through a mask, etc. for forming a pattern. The exposure amount can be appropriately determined and it is usually from 1 to 100 mJ/cm$^2$. After the exposure, spinning and/or baking is preferably conducted, development and rinsing are carried out to obtain a pattern. Preferably, baking is conducted after the exposure, and the temperature for the baking is usually from 30 to 300° C. With a view point of PED described above, it is preferred that the period of time from the exposure to the baking step is shorter.

The light for the exposure is far ultraviolet rays at a wavelength preferably of 250 nm or less, more preferably, 220 nm or less. Specifically, they include KrF excimer laser (248 nm), ArF excimer laser (193 nm) $F_2$ excimer laser (157 nm) and X rays, etc.

Incidentally, the change in performance of the resist when being subjected to the liquid immersion exposure is thought to be due to the contact between the surface of the resist and the liquid immersion solution.

The liquid immersion solution used upon liquid immersion exposure is to be described below.

The liquid immersion solution is preferably a liquid which is transparent to the exposure wavelength and having a temperature coefficient of the refractive index as small as possible such that the strength of the optical images projected on the resist is minimized. Particularly, in a case where the exposure light source is an ArF excimer laser (wavelength: 193 nm), use of water is preferred in view of easy availability and easy handling in addition to the view points described above.

For the purpose of further improvement of refraction index, medium having refraction index of 1.5 or more may be used.

In a case of using water as the liquid immersion solution, an additive (liquid) that does not dissolve the resist layer on the wafer and the effect of which to the optical coating at the lower surface of the lens device is negligible may be added at a slight ratio in order to decrease the surface tension of water and increase the surface activity. The additive is preferably an aliphatic alcohol having the refractive index substantially equal with that of water and, specifically, it includes, for example, methyl alcohol, ethyl alcohol, isopropyl alcohol, etc. The addition of the alcohol of the refractive index substantially equal with that of water can provide a merit capable of decreasing the change of the refractive index as less as possible as the entire liquid even when the alcohol ingredient in water is evaporated to change the concentration of the content. On the other hand, in a case where a substance not transparent to a light at 193 nm or impurities having a refractive index greatly different from that of water should be mixed, since this causes distortion in the optical images projected over the resist, distilled water is preferred as water to be used. Further, purified water filtered by passing through an ion exchange filter or the like may also be used.

The electric resistance of water is preferably 18.3 MΩ·cm or more and the TOC (organic material concentration) is preferably 20 ppb or less. Further, deaeration is applied preferably.

The lithography performance can be improved by elevating the refraction index of the liquid immersion solution. In view of this, additive for elevating the refraction index can be added in water, or heavy water ($D_2O$) may be used instead of water.

A film less soluble to the liquid immersion solution may also be disposed between the resist film formed of the positive type resist for use in the liquid immersion exposure and the liquid immersion solution of the invention (hereinafter referred to as "top coat"), in order to avoid direct contact of the resist film with the liquid immersion solution. The function necessary for the top coating is the coating adaptability to the portion to the upper layer portion of the resist, transparency to radioactive rays, particularly, at 193 nm, and less solubility to the liquid immersion solution. It is preferred the top coat is immiscible with the resist and, further, can be coated uniformly to the upper layer of the resist.

A polymer not containing the aromatic ingredient is preferred for the top coat in view of the transparency at 193 nm and includes, for example, a hydrocarbon polymer acrylate ester polymer, polymethacrylic acid, polyacrylic acid, polyvinyl ether, silicon-containing polymer, and fluorine-containing polymer.

When the top coat is peeled, a liquid developer may be used or a peeling agent may be used separately. As the peeling agent, a solvent with less penetration to the resist is preferred. It is preferred that the resist can be peeled by the alkali developer in that the peeling step can be applied simultaneously with the developing step for the resist. With a view point of peeling by the alkali developer, the top coat is preferably acidic and with a view point of non-intermixing property with the resist, it may be either neutral or alkaline.

The resolution is improved in a case where there is no difference of the refractive index between the top coating and the liquid immersion solution. In a case of using an ArF excimer layer (wavelength: 193 nm) as the exposure light source, since the use of water as the liquid immersion solution is preferred, it is preferred that the refractive index of the top coating for use in ArF liquid immersion exposure is similar with that of water (1.44). Further, with a view point of transparency and refractive index, a thin film is more preferred.

In the case of using organic solvent as the liquid immersion solution, the top coating is preferably water-soluble.

As the alkali developer to be used in the developing step, there can be used, for example, inorganic alkalis such as sodium hydroxide, potassium hydroxide, sodium carbonate, sodium silicate, sodium metasilicate, and aqueous ammonia, primary amines such as ethylamine and n-propylamine, secondary amines such as diethylamine and di-n-butyl amine, tertiary amines such as triethylamine and methyldiethyl amine, alcohol amines such as dimethyl ethanolamine and triethanolamine, quaternary ammonium salts such as tetramethyl ammonium hydroxide and tetraethyl ammonium hydroxide, and aqueous alkaline solution such as pyrrol and piperidine.

Further, the aqueous alkaline solutions may also be used with addition of an appropriate amount of alcohol or surfactant.

As a rinsing solution, purified water is used and it may also be used with addition of an appropriate amount of surfactant.

The alkali concentration of the alkali developer is usually from 0.1 to 20 mass %.

The pH of the alkali developer is usually from 10.0 to 15.0.

After the developing treatment or the rinsing treatment, a treatment of removing the developer or the rinsing solution deposited on the pattern can be conducted with a supercritical fluid.

EXAMPLE

The invention is to be described more specifically by way of examples, but the content of the invention is not restricted to them.

Synthesis of Resin (1)

2-adamantyl-2-propylmethacrylate, 3,5-dihydroxy-1-adamantyl methacrylate and norbornane lactone acrylate at a molar ratio of 40/20/40 (molar ratio) and dissolved in propylene glycol monomethyl ether acetate/propylene glycol monomethyl ether=40/40 (mass ratio) to prepare 450 g of a solution with 22% solid concentration. To the solution, 1 mol % of a polymerization initiator, V-601 (dimethyl 2,2'-azobis (2-methylpropionate) available from WAKO JUNYAKU KOGYO CO. was added, which was added dropwise under a nitrogen atmosphere to 50 g of a mixed solution of propylene glycol monomethyl ether acetate/propylene glycol monomethyl ether=60/40 (mass ratio) heated to 100° C. over 6 hours. After the completion of addition, the reaction solution was stirred for 2 hours. After the completion of the reaction, the reaction solution was cooled to a room temperature, a white powder crystallized and deposited on 5 L of a mixed medium of hexane/ethyl acetate=9/1 (mass ratio) was obtained through filtration to recover the aimed resin (1). By $^{13}$CNMR and polymer acid value measurement, the polymer compositional ratio (2-adamantyl-2-propylmethacrylate/3,5-dihydroxy-1-adamantyl methacrylate/norbornane lactone acrylate (a/b/c) was determined as 39/21/40 (molar ratio). As a result of GPC measurement, the weight average molecular weight (Mw) on the basis of standard polystyrene was 9700, and the degree of dispersion (Mw/Mn) was 2.01.

The resins (2) to (20) which were used in the invention were synthesized in the same manner as the method for the resin (1).

The structures of the resins (1) to (20) are described below.

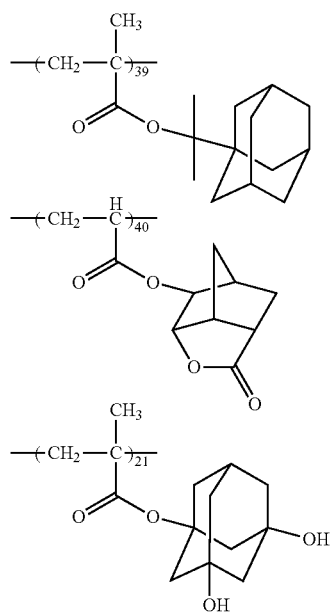

Mw = 9700
Mw/Mn = 2.01

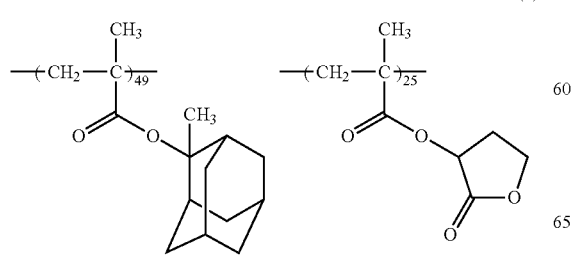

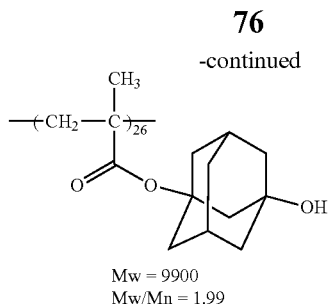

Mw = 9900
Mw/Mn = 1.99

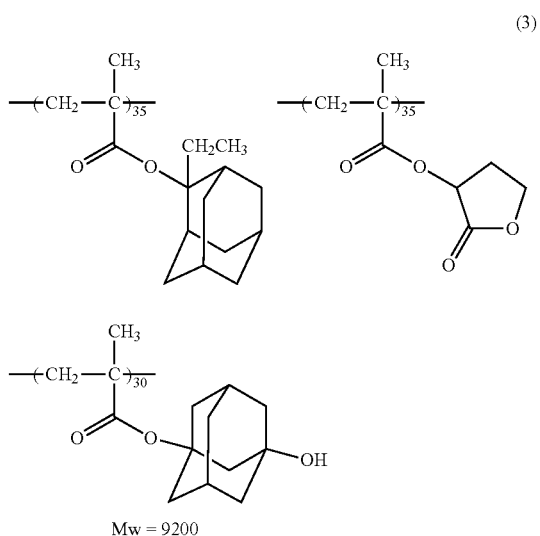

Mw = 9200
Mw/Mn = 2.04

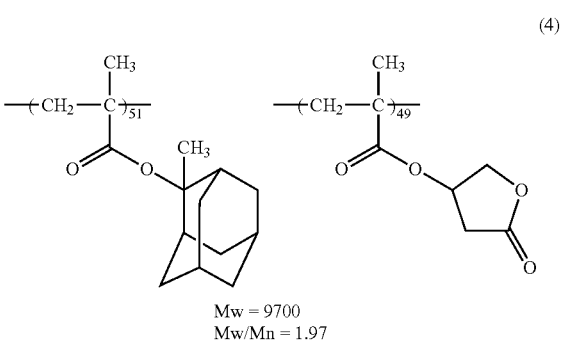

Mw = 9700
Mw/Mn = 1.97

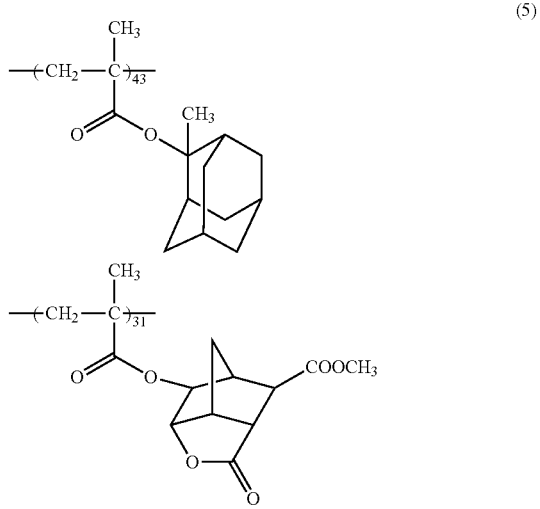

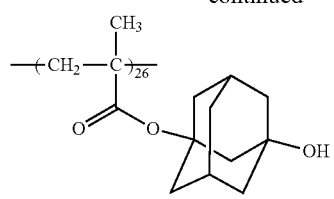
Mw = 8200
Mw/Mn = 1.91
(6)
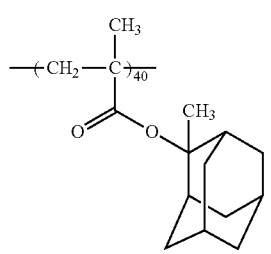
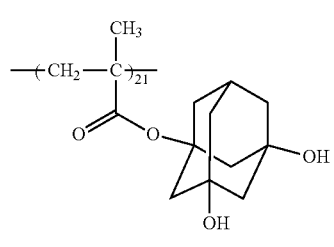
Mw = 9500
Mw/Mn = 2.07
(7)
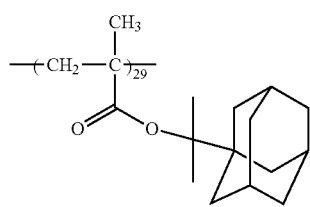
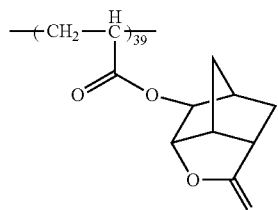
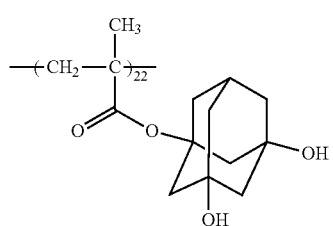
Mw = 8700
Mw/Mn = 1.98
(8)
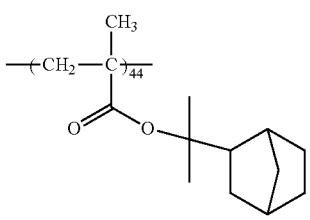
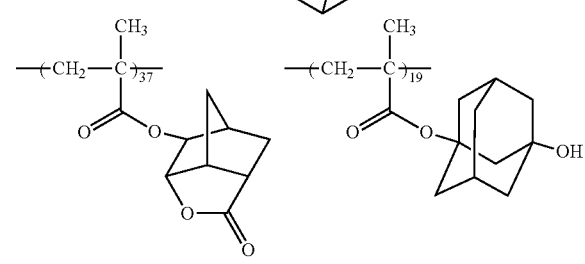
Mw = 10300
Mw/Mn = 2.16
(9)
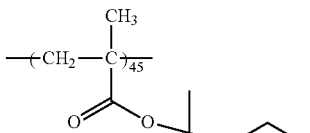
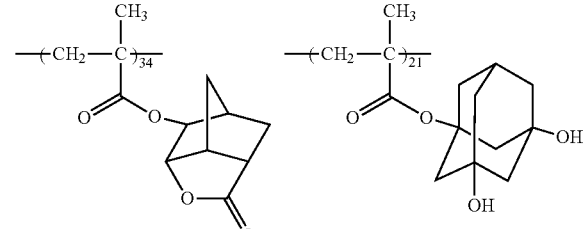
Mw = 11300
Mw/Mn = 2.21
(10)
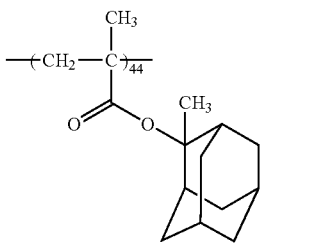
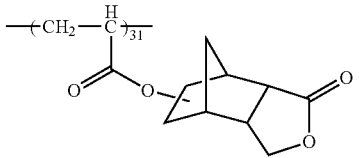
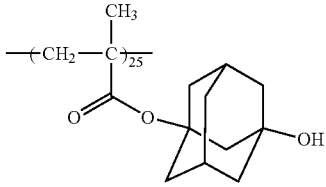
Mw = 8300
Mw/Mn = 1.97

-continued
(11)
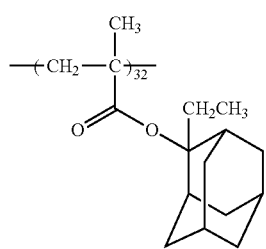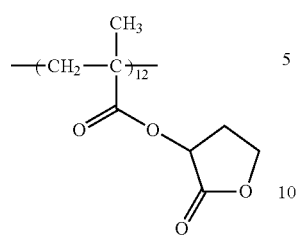
(13)
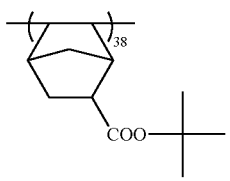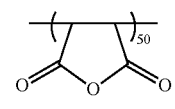
Mw = 7100
Mw/Mn = 2.42
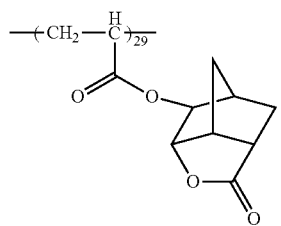
(14)
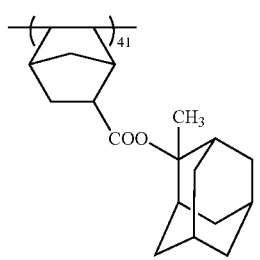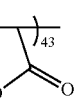
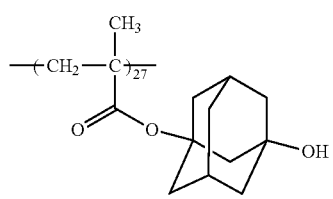
Mw = 10200
Mw/Mn = 2.31
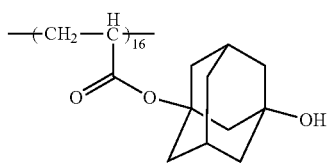
Mw = 8900
Mw/Mn = 2.19
(12)
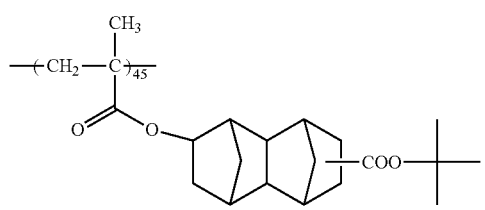
(15)
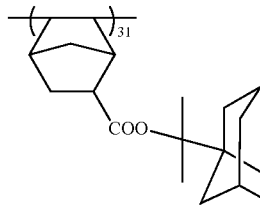
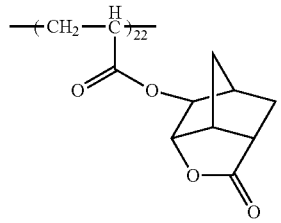
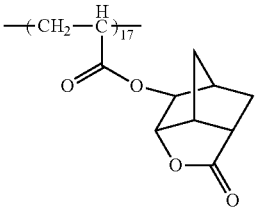
Mw = 11100
Mw/Mn = 2.37
(16)
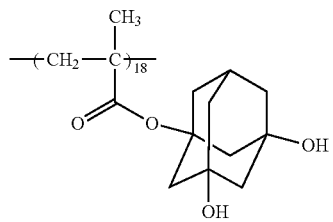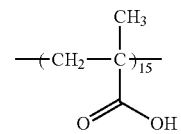
Mw = 8700
Mw/Mn = 2.23
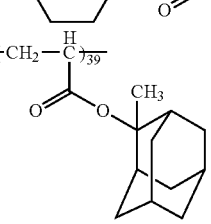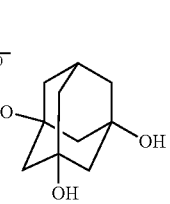
Mw = 10400
Mw/Mn = 2.51

-continued

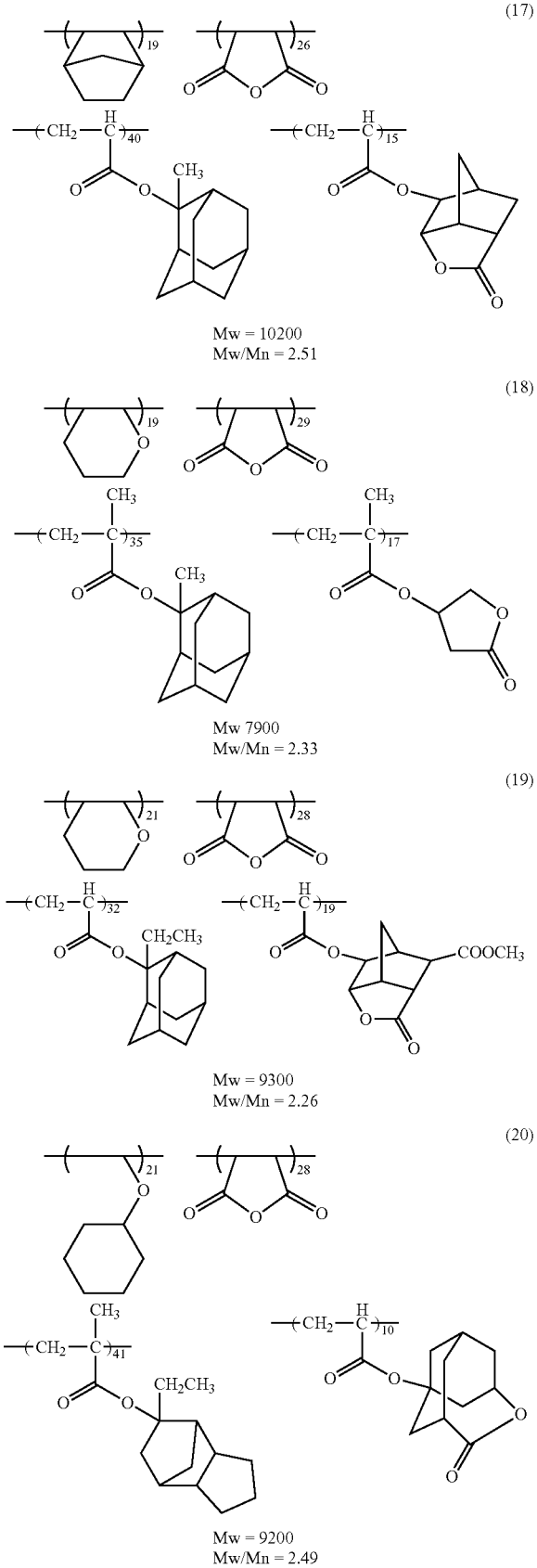

Examples 1 to 27 and Comparative Examples 1 to 4

Preparation of Resist

Ingredients shown in the Table 1 were dissolved each in solvent to prepare solutions at 10 mass % concentration for solid content, and filtered through a 0.1 µm polyethylene filter to prepare positive type resist compositions for use in liquid immersion exposure. Each of the positive type resist compositions for use in the liquid immersion exposure thus prepared was evaluated by the following method and the results are shown in Table 1. When the ingredients are used in plurality, the ratio between them is expressed by mass ratio.

An organic antireflection film ARC 29A (manufactured by Nissan Chemical Co.) was coated over a silicon wafer, and baked at 205° C. for 60 sec to form an anti-reflection film at 78 nm. A positive type resist composition for use in liquid immersion exposure thus prepared was coated, and baked at 120° C. for 60 sec to form a resist film of 150 nm. The thus obtained wafer was put to 2-beam interference exposure by a device shown in FIG. 1 using pure water as the liquid immersion solution (wet exposure). The wavelength of the laser used was 193 nm, and a prism forming a 90 nm line & space pattern was used. Just after exposure, it was heated at 125° C. for 90 sec and then developed with an aqueous solution of tetramethyl ammonium hydroxide (2.38 mass %) for 60 sec, rinsed with pure water and then spin-dried to obtain a resist pattern.

In the apparatus shown in FIG. 1, are shown a laser 1, a diaphragm 2, a shutter 3, reflection mirrors 4, 5, and 6, a condensing lens 7, a prism 8, a liquid immersion solution 9, a wafer 10 provided with an anti-reflection film and a resist film, and a water stage 11.

<Evaluation Method>
[Development Defect]

Number of development defects was measured for the resist pattern obtained as described above by using KLA-2360 apparatus manufactured by KLA Tencor Japan and the obtained primary data values were used as the result of measurement.

[Scum]

The remaining state of development residues in a resist pattern of 90 mm line width obtained as described above (scums) was observed by a scanning type electron microscope (S-9260, manufactured by Hitachi) and evaluated as A for those not observed with residues, as C for those observed with considerable residues and as B for those therebetween.

[Leaching Amount of Generated Acid]

The prepared resist composition was coated on a 8 inch silicon wafer, and baked at 115° C. for 60 sec to form a resist film of 150 nm. After exposing the resist film by an exposure apparatus at a wavelength of 193 nm for the entire surface at 50 mJ/cm$^2$ and then 5 ml of pure water deionized by using a super pure water manufacturing apparatus (Milli-QJr, manufactured by NIPPON MILLIPORE) was dropped on the resist film. After placing water, on the resist film for 50 sec, the water was sampled, and the concentration of the acid leached therein was determined by LC-MS.

LC apparatus: 2695, manufactured by Water Co.
MS apparatus: Esquire 3000 plus manufactured by Bruke Kaltonics. Co.

The concentration of the leached anion species of the photoacid generator (PAG) was measured by the LC-MS apparatus.

TABLE 1

| | | Composition | | | | | | Evaluation | | |
|---|---|---|---|---|---|---|---|---|---|---|
| | | Resin (2 g) | Photo acid generator (mg) | Solvent (mass ratio) | Surfactant (5 mg) | Dissolution inhibitive compound (g) | Alkali soluble compound (C) | Number of defects | Scum | Leaching degree (%) |
| Example | 1 | 1 | z2(20) | SL-4/SL-6 (60/40) | W-1 | — | (E-1) | 300 | A | 5 |
| | 2 | 2 | z2(24) | SL-2/SL-4 (50/50) | W-2 | — | (D-1) | 310 | A | 6 |
| | 3 | 3 | z6(28) | SL-1/SL-4/SL-8 (40/58/2) | W-3 | — | (E-4) | 320 | A | 7 |
| | 4 | 4 | z1(20) | SL-2/SL-4 (40/60) | W-4 | — | (E-2) | 310 | A | 6 |
| | 5 | 5 | z2(20) | SL-2/SL-4 (40/60) | — | — | (D-2) | 300 | A | 5 |
| | 6 | 6 | z6(20) | SL-2/SL-4/SL-9 (40/59/1) | W-4 | — | (E-1)/(D-2) (10/90) | 330 | A | 7 |
| | 7 | 7 | z6(20) z9(15) | SL-2/SL-4 (50/50) | W-1 | — | (D-1)/(E-7) (50/50) | 310 | A | 8 |
| | 8 | 8 | z38(20) | SL-2/SL-6 (70/30) | W-1 | — | (D-4) | 360 | B | 12 |
| | 9 | 9 | z2(30) | SL-2/SL-4/SL-9 (40/59/1) | W-1 | — | (E-1) | 310 | A | 6 |
| | 10 | 10 | z2(25) | SL-2/SL-4 (40/60) | W-2 | — | (D-1)/(D-5) (70/30) | 300 | B | 8 |
| | 11 | 11 | z38(12) z2(25) | SL-2/SL-4 (40/60) | W-3 | — | (E-1)/(E-7) (90/10) | 330 | A | 7 |
| | 12 | 12 | z6(12) z31(10) | SL-2/SL-4 (40/60) | W-4 | — | (D-1)/(D-3) (70/30) | 270 | A | 2 |
| | 13 | 13 | z6(22) z25(10) | SL-1/SL-7 (40/60) | W-4 | I-1 (0.1) | (D-3) | 280 | A | 3 |
| | 14 | 14 | z2(32) | SL-4/SL-6 (60/40) | W-1 | — | (E-22) | 320 | A | 7 |
| | 15 | 15 | x38(40) | SL-3/SL-7 (60/40) | W-3 | — | (D-1)/(D-2) (70/30) | 310 | A | 8 |
| | 16 | 16 | z3(33) | SL-2/SL-5 (60/40) | W-2 | — | (D-1)/(E-7) (20/80) | 310 | A | 6 |
| | 17 | 17 | z2(50) | SL-2/SL-7 (60/40) | W-2 | I-2 (0.1) | (D-4) | 350 | B | 13 |
| | 18 | 18 | z38(27) | SL-2/SL-7 (60/40) | W-1 | — | (D-3) | 280 | A | 2 |
| | 19 | 19 | z6(29) | SL-2/SL-7 (60/40) | W-1 | — | (D-1)/(D-2) (80/20) | 310 | A | 6 |
| | 20 | 20 | z3(25) | SL-2/SL-4 (40/60) | W-4 | — | (D-3) | 300 | A | 5 |
| | 21 | 1 | z55(100) | SL-2/SL-4 (40/60) | W-1 | — | (D-6) | 270 | A | 8 |
| | 22 | 2 | z55(80) | SL-2/SL-4 (30/70) | W-1 | — | (D-7) | 310 | A | 5 |
| | 23 | 1 | z56(20) z14(10) | SL-4/SL-6 (60/40) | W-2 | — | (D-8) | 300 | A | 8 |
| | 24 | 1 | z34(120) | SL-2/SL-4 (30/70) | W-2 | — | (D-9) | 280 | A | 6 |
| | 25 | 2 | z60(5) z67(40) | SL-2/SL-4 (40/60) | W-1 | — | (D-9) | 280 | A | 6 |
| | 26 | 2 | z67(40) | SL-2/SL-4 (40/60) | W-1 | — | (D-9) | 280 | A | 8 |
| | 27 | 1 | z55(30) z60(10) | SL-4/SL-6 (60/40) | W-4 | — | (D-10) | 300 | A | 8 |
| Comparative Example | 1 | 1 | z2(24) | SL-4/SL-6 (60/40) | W-1 | — | — | 650 | C | 30 |
| | 2 | 2 | z2(24) | SL-2/SL-4 (60/40) | W-1 | — | — | 670 | C | 32 |
| | 3 | 3 | z2(24) | SL-4/SL-6 (60/40) | W-1 | — | — | 620 | C | 35 |
| | 4 | 4 | z2(24) | SL-4/SL-6 (60/40) | W-1 | — | — | 650 | C | 33 |

The symbols in Table 1 are as follows.
Acid generators correspond to those exemplified above.
SL-1: cyclopentanone
SL-2: cyclohexanone
SL-3: 2-methylcyclohexanone
SL-4: propylene glycol monomethyl ether acetate
SL-5: ethyl lactate
SL-6: propylene glycol monomethyl ether
SL-7: 2-heptanone
SL-8: γ-butyrolactone
SL-9: propylene carbonate
W-1: Megafac F176, (manufactured by Dainippon Ink and Chemicals, Inc.) (Fluoro type)
W-2: Megafac R08, (manufactured by Dainippon Ink and Chemicals, Inc.) (Fluoro and silicon type)
W-3: Polysiloxane polymer KP-341 (manufactured by Shin-Etsu Chemical Co., Ltd.) (Silicon type)

W-4: Troysol S-366 (manufactured by Troy Chemical Industries, Inc.).
I-1: t-butyl lithocholate
I-2: t-butyl adamantane carboxylate
[Low Molecular Alkali Soluble Compound]
E-1: A compound having an alkali soluble group exemplified above, with an acid value of 2.6 mm equivalent/g.
E-2: A compound having an alkali soluble group exemplified above, with an acid value of 2.4 mm equivalent/g.
E-4: A compound having an alkali soluble group exemplified above, with an acid value of 5.0 mm equivalent/g.
E-7: A compound having an alkali soluble group exemplified above, with an acid value of 3.6 mm equivalent/g.
E-22: A compound having an alkali soluble group exemplified above formed by hydrolysis by the alkali developer exemplified above, with an acid value of 0.0 mm equivalent/g.
[High Molecular Alkali Soluble Compound]
(D-1) to (D-10): High molecular alkali soluble compounds shown in Table 2 (resins).

The repetitive unit constitutions (C-1), (C-7), (C-19), (C-23) and (C-31) to (C-33) in Table 2 mean repetitive unit constitutions of the alkali soluble compounds exemplified above (resins). The compositional ratios are molar ratios of the repetitive units. The unit of the acid value is mm equivalent/g.

| Alkali soluble compound | Constitution of repetitive units | Compositional ratio | Molecular weight | Dispersion degree | Acid value |
|---|---|---|---|---|---|
| (D-1) | (C-1) | 50/50 | 10000 | 1.4 | 3.9 |
| (D-2) | (C-1) | 70/30 | 15000 | 1.4 | 6.3 |
| (D-3) | (C-7) | 50/50 | 8000 | 1.3 | 1.6 |
| (D-4) | (C-19) | 50/50 | 8000 | 1.4 | 2.4 |
| (D-5) | (C-23) | 50/50 | 8000 | 1.3 | 2.8 |
| (D-6) | (C-31) | 80/20 | 12000 | 2.1 | 4.4 |
| (D-7) | (C-31) | 60/40 | 5000 | 1.8 | 3.1 |
| (D-8) | (C-32) | 70/30 | 12000 | 1.5 | 2.0 |
| (D-9) | (C-33) | 80/20 | 7000 | 1.7 | 2.0 |
| (D-10) | (C-33) | 60/40 | 7000 | 1.8 | 1.6 |

The results of Table 1 show that, upon liquid immersion exposure, the positive type resist composition for liquid immersion exposure according to the invention has small number of development defects and scum, and that the leaching thereof to the liquid immersion solution is suppressed.

The present invention can provide a positive type resist composition suitable to liquid immersion exposure suppressing development defects, scums and leaching of the resist ingredient to the liquid immersion solution during liquid immersion exposure, as well as a method of forming a pattern using the same.

The entire disclosure of each and every foreign patent application from which the benefit of foreign priority has been claimed in the present application is incorporated herein by reference, as if fully set forth.

What is claimed is:

1. A resist composition for ArF exposure, comprising:
   (A) a resin having a monocyclic or polycyclic cycloaliphatic hydrocarbon structure, the resin increasing its solubility in an alkali developer by an action of acid;
   (B) a compound generating acid upon irradiation with one of an actinic ray and a radiation;
   (C) a resin containing an alkyl group having 2 or more carbon atoms; and
   (D) a solvent,
   wherein the structure of resin (A) and the structure of resin (C) are not in the same compound,
   a content of the resin (C) is 1 to 10 mass % on the basis of the total solid content of the resist composition,
   the resin (C) contains an alkali soluble group, and
   the resin (C) contains a fluorine atom.

2. The resist composition for ArF exposure according to claim 1,
   wherein the resin (C) contains an unsubstituted alkyl group having 2 to 20 carbon atoms.

3. The resist composition for ArF exposure according to claim 2,
   wherein the resin (C) contains a repeating unit derived from a (meth)acrylic acid derivative having an substituted alkyl group having 2 to 20 carbon atoms.

4. The resist composition for ArF exposure according to claim 3,
   wherein the resin (A) contains a lactone group.

5. The resist composition for ArF exposure according to claim 4,
   wherein the resin (A) contains no aromatic group.

6. The resist composition for ArF exposure according to claim 1,
   wherein the resin (C) contains an alkyl group having 5 or more carbon atoms.

7. The resist composition for ArF exposure according to claim 6,
   wherein the resin (C) contains a fluorinated alkyl group having 5 or more carbon atoms.

8. The resist composition for ArF exposure according to claim 1,
   wherein the resin (C) contains a carboxyl group as the alkali soluble group.

9. The resist composition for ArF exposure according to claim 1,
   wherein the resin (C) contains a fluorinated alcohol as the alkali soluble group.

10. The resist composition for ArF exposure according to claim 6,
    wherein the resin (C) contains a group which is solubilized by hydrolyzation with an alkali developer.

11. The resist composition for ArF exposure according to claim 10,
    wherein the resin (C) contains a lactone group as the group which is solubilized by hydrolyzation with an alkali developer.

12. The resist composition for ArF exposure according to claim 10,
    wherein the resin (C) contains an ester group as the group which is solubilized by hydrolyzation with an alkali developer.

13. The resist composition for ArF exposure according to claim 10,
    wherein the resin (C) contains a sulfone amide group as the group which is solubilized by hydrolyzation with an alkali developer.

14. A resist film formed by using the resist composition for ArF exposure according to claim 1.

15. A pattern forming method, comprising exposing the resist film according to claim 14 with an ArF excimer laser.

16. The pattern forming method according to claim 15, wherein the exposing is an immersion exposure.

* * * * *